US010817057B2

(12) United States Patent
Takahashi

(10) Patent No.: US 10,817,057 B2
(45) Date of Patent: Oct. 27, 2020

(54) INFORMATION PROCESSING DEVICE, INFORMATION PROCESSING METHOD, AND PROGRAM

(71) Applicant: SONY CORPORATION, Tokyo (JP)

(72) Inventor: Shuichi Takahashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/339,306

(22) PCT Filed: Oct. 23, 2017

(86) PCT No.: PCT/JP2017/038213
§ 371 (c)(1),
(2) Date: Apr. 3, 2019

(87) PCT Pub. No.: WO2018/088187
PCT Pub. Date: May 17, 2018

(65) Prior Publication Data
US 2020/0042090 A1    Feb. 6, 2020

(30) Foreign Application Priority Data
Nov. 8, 2016  (JP) ................ 2016-217805

(51) Int. Cl.
G06F 3/01     (2006.01)
H04N 13/117   (2018.01)
G06K 9/32     (2006.01)

(52) U.S. Cl.
CPC ........... G06F 3/015 (2013.01); G06K 9/3233 (2013.01); H04N 13/117 (2018.05)

(58) Field of Classification Search
CPC .... H04N 21/442; H04N 13/117; A61B 5/107; A61B 5/16; A61B 5/0488; A61B 5/0476;
(Continued)

(56) References Cited

U.S. PATENT DOCUMENTS

2009/0247895 A1   10/2009  Morikawa et al.
2011/0071416 A1    3/2011  Terada et al.
(Continued)

FOREIGN PATENT DOCUMENTS

CN   101589358 A   11/2009
CN   102099770 A    6/2011
(Continued)

OTHER PUBLICATIONS

International Search Report and Written Opinion of PCT Application No. PCT/JP2017/038213, dated Jan. 23, 2018, 16 pages of ISRWO.

*Primary Examiner* — Muhammad N Edun
(74) *Attorney, Agent, or Firm* — Chip Law Group

(57) ABSTRACT

Image assessment information is generated, and analysis information such as the degree of interest in an image presented to the user or a region of interest is acquired on the basis of a brainwave signal of a user observing an image. A content delivery unit that delivers image content, a data transceiver unit that receives delivery content, a head-mounted display that presents content, and a content analysis unit that analyzes content assessment information are included. The data transceiver unit generates assessment information set to be able to identify whether a brainwave signal is output when a certain image is presented in association with the brainwave signal and image reproduction control information acquired from the user and outputs the assessment information to a content analysis device. The content analysis device analyzes the degree of interest in the image presented to the user, a region of interest, or the like using the brainwave signal.

15 Claims, 14 Drawing Sheets

(58) Field of Classification Search
CPC .... A61B 5/0484; G06K 9/3233; G06F 13/00; G06F 3/015
See application file for complete search history.

(56) References Cited

U.S. PATENT DOCUMENTS

| | | | | |
|---|---|---|---|---|
| 2014/0108309 | A1* | 4/2014 | Frank | G06Q 10/00 706/12 |
| 2016/0109851 | A1* | 4/2016 | Tsang | G03H 1/0866 359/9 |
| 2017/0017080 | A1* | 1/2017 | Onwuta | G02B 27/017 |
| 2017/0259167 | A1* | 9/2017 | Cook | A63F 13/24 |

FOREIGN PATENT DOCUMENTS

| | | |
|---|---|---|
| JP | 07-061325 A | 3/1995 |
| JP | 07-61325 B2 | 7/1995 |
| JP | 2011-120824 A | 6/2011 |
| JP | 2013-258555 A | 12/2013 |
| JP | 5624512 B2 | 11/2014 |
| RU | 2009104463 A | 8/2010 |
| WO | 2008/059878 A1 | 5/2008 |
| WO | 2008/059787 A1 | 3/2010 |
| WO | 2010/082496 A1 | 7/2010 |
| WO | 2010/082496 A1 | 7/2012 |

* cited by examiner

INFORMATION PROCESSING DEVICE, INFORMATION PROCESSING METHOD, AND PROGRAM

CROSS REFERENCE TO RELATED APPLICATIONS

This application is a U.S. National Phase of International Patent Application No. PCT/JP2017/038213 filed on Oct. 23, 2017, which claims priority benefit of Japanese Patent Application No. JP 2016-217805 filed in the Japan Patent Office on Nov. 8, 2016. Each of the above-referenced applications is hereby incorporated herein by reference in its entirety.

TECHNICAL FIELD

The present disclosure relates to an information processing device, an information processing method, and a program, and more particularly, to an information processing device, an information processing method, and a program capable of, for example, presenting an image to a user (viewer) and analyzing a region of interest, a degree of interest, a degree of concentration, a degree of fatigue, and the like of the user with regard to an image on the basis of brainwaves of the user (user (viewer)).

BACKGROUND ART

In recent years, various kinds of content such as game content and movie content have been supplied to many users (viewers) through, for example, networks, broadcasts, or media.

Content deliverers acquire assessments of users of delivery content to use the assessments in subsequent development of content in many cases.

As a general scheme of acquiring user assessments of delivery content, for example, there are questionnaires. However, questionnaire processing has a problem that time or cost increases and each user may not necessarily make an honest assessment.

Further, in a case in which delivery content is moving image content, there are problems that it is difficult to analyze in which part each user (viewer) is interested in each frame included in content, that is, a region of interest, from questionnaire and it is difficult to analyze or assess an image region that a user finds highly interesting.

For example, processes of assessing images or content can be classified into an objective assessment process and a subjective assessment process.

The subjective assessment process is a process in which the user (viewer) intuitively assesses observation target content. The objective assessment process is an assessment process executed by removing such personal subjectivity.

At present, for example, various studies for improving quality of images are under way. An improvement in subjective assessment for an image quality is one of the elements to be considered when an image quality improvement technologies or compression encoding technologies for images are developed.

As subjective schemes for image quality assessment, for example, there are the following various assessment schemes executed together by experts or non-experts of image processing:

n-stage assessment (MOS: Mean Opinion Score), (where n=5, 7, or the like);

score assessment (magnitude estimation method or the like); and introspective assessment (comment recording).

These schemes are subjective schemes of executing an image quality assessment process by replacing feelings of images viewed by experts or non-experts of image processing with numbers or text.

However, the subjective assessment processes have the following problems:

(1) results are irregular for each individual because of subjective assessment;

(2) since assessment axes are designated, items deviating from the axes are not assessed;

(3) assessment results are considerably influenced by experience or knowledge of users (viewers); and (4) many users (viewers) are necessary and time and cost are required to guarantee precision of results.

For example, there are the foregoing problems.

To solve the problems, it is necessary to execute assessment objectively.

Here, when an objective assessment result deviates from a subjective assessment result, there is no meaning.

Accordingly, it is important to generate an objective assessment result which does not deviate from a subjective assessment result.

As an objective scheme for image quality assessment, peak signal-to-noise ratio (PSNR) and structural similarity index measure (SSIM) are known.

Both the schemes are schemes of outputting image quality assessment values as objective numerical values.

However, a case in which numerical values obtained as image quality assessment values by the foregoing PSNR and SSIM do not match actual feelings of image viewers is pointed out, and thus subjective assessment is not yet replaced completely.

To solve the problem, a study for an objective assessment scheme for an image quality or content using brainwaves of image observers has recently been carried out.

The assessment scheme using brainwaves is configured to detect how users (viewers) viewing assessment target images feel by monitoring changes in the brainwaves.

It is considered that a human feeling or a kind of stimulus presented to an image observer can be inferred from a brainwave by linking a brainwave of the image observer which is an objective assessment result with an actual feeling based on a subjective assessment result of the image observer.

However, this scheme has the following problems:

(1) cost and training are necessary to introduce and administrate a device; and (2) this scheme is more complicated than the above-described objective assessment scheme since electrodes are worn on a user (viewer) at the present time.

However, it is considered that results which are rarely influenced by knowledge or experience of a user (viewer) and assessment axes can be obtained.

In addition, by synchronizing a presentation timing of an image with a recording timing of a brainwave, it is possible to record when and what a subject feels.

As examples of the related art in which image assessment structures using brainwaves are disclosed, for example, there are Patent Literature 1 (JP 2013-258555A), Patent Literature 2 (JP H07-061325B), Patent Literature 3 (JP 5624512B).

Patent Literature 1 describes a head-mounted display that acquires information such as brainwaves, bloodstreams, pulsation, and a visual line of a user (viewer) observing a game image, ascertains a mental state of the user playing a game on the basis of the information to reflect the mental state in development of the game, or detects the degree of tension of the user playing the game.

Patent Literature 1 discloses a configuration in which, on the basis of mental states acquired from users (viewers) and analyzed, a process of updating game content to be displayed or a control process of causing development of a game of all the game players to be changed moment by moment in accordance with a mental state of each user is performed when the game is shared among the plurality of game players.

Patent Literature 2 discloses a device that assesses interest of a user (viewer) in a visual stimulus by presenting the visual stimulus with a predetermined frequency (for example, 10 Hz) to the user (viewer) who is an image observer and measuring a change in the measured magnitude of a brainwave frequency component of the user (viewer).

More specifically, a response to the visual stimulus is assessed by measuring a change in a steady-state visual evoked potential during presentation of the visual stimulus.

Patent Literature 3 discloses a device that acquires a cerebral bloodstream volume and a visual line position of a user at the time of viewing of image content, identifies a psychological response to the image content or calculates the degree of interest of the user in the image content (the degree of interest), and decides assessment of the image content. Note that a change in a cerebral bloodstream indicates a change in cerebral activity as in a change in brainwaves.

CITATION LIST

Patent Literature

Patent Literature 1: JP 2013-258555A
Patent Literature 2: JP H07-061325B
Patent Literature 3: JP 5624512B

DISCLOSURE OF INVENTION

Technical Problem

The configuration of Patent Literature 1 described above is a configuration in which only brainwaves of a frontal region are an acquisition and analysis target and there is a problem that precision of measurement for a mental state of a user is limited.

In addition, Patent Literature 1 discloses a configuration in which a visual line direction, a motion of a pupil, a frequency of blinking, or the like of a user is detected and converted into a psychological state index of the user in accordance with a conversion expression. An image sensor is used to detect a visual line direction, a motion of a pupil, a frequency of blinking, or the like, and thus there is a problem that it is difficult to include the image sensor in a general viewing device for a user, for example, a head-mounted display, in terms of cost.

In addition, Patent Literature 2 discloses a configuration in which a steady-state visual evoked potential during presentation of visual stimuli (=images) is measured and interest of a user (viewer) is assessed on the basis of a change in a specific frequency component. In this configuration, however, when a change in the average luminance of the stimuli (images) appears as a change in a frequency component, the interest of the user (viewer) may not be assessed. Therefore, it is necessary to constantly maintain average luminance of the stimulus (image).

However, a lengthy moving image also contains many scene changes. Thus, there are problems that it is difficult to constantly maintain the average luminance and it is difficult to obtain accurate user assessment.

Patent Literature 3 discloses a configuration in which a cerebral bloodstream is detected to measure brain activity. In the detection of the cerebral bloodstream, there is a scheme of radiating infrared light and analyzing a pattern of its reflected light and there is also a device called a near infra-red spectoroscopy (NIRS) using this scheme. However, the NIRS is very expensive and there is a problem that it is difficult to include the NIRS in a general viewing device only for a user, for example, a head-mounted display, in terms of cost.

The present disclosure is devised, for example, in view of the foregoing problems and an object of the present disclosure is to provide an information processing device, an information processing method, and a program which can be included in a general viewing device only for a user, for example, a head-mounted display (HMD), and is capable of analyzing a region of interest, a degree of interest, a degree of concentration, a degree of fatigue, and the like of a user with regard to an image configured as content in an inexpensive configuration.

Solution to Problem

A first aspect of the present disclosure is an information processing device of a head-mounted display including: an image presentation unit configured to present an image to a user (viewer); and a brainwave measurement unit configured to measure a brainwave of the user (viewer). A brainwave measurement electrode is set in a region of a head of the user (viewer) on which the head-mounted display is worn.

A second aspect of the present disclosure is an information processing device that generates assessment information set to enable identification of whether a brainwave signal is output when a certain image is presented in association with the brainwave signal acquired from a user (viewer) observing the image and reproduction control information of the image.

A third aspect of the present disclosure is an information processing device. A brainwave signal acquired from a user (viewer) observing an image and assessment information which is data corresponding to reproduction control information of the image and is set to enable identification of whether the brainwave signal is output when a certain image is presented are input, and an analysis process of acquiring a degree of interest in the image presented to the user (viewer) or at least one piece of information among assessment, a degree of concentration, and a degree of fatigue is executed using assessment information including the brainwave signal.

A fourth aspect of the present disclosure is an information processing device, in which image content to be presented to a user (viewer) is delivered, and control of the delivery content is executed in accordance with an analysis result based on a brainwave signal acquired from the user (viewer) observing an image.

A fifth aspect of the present disclosure is an information processing system including: a user device that presents content to a user (viewer); and a content analysis device that receives assessment information regarding the content from the user device and analyzes the assessment information, in which the user device generates assessment information set to enable identification of whether a brainwave signal is output when a certain image is presented in association with the brainwave signal acquired from the user (viewer) observing the image and reproduction control information of the image, and outputs the assessment information to the content analysis device.

A sixth aspect of the present disclosure is an information processing method executed in an information processing device, in which a data processing unit of the information processing device generates assessment information set to enable identification of whether a brainwave signal is output when a certain image is presented in association with the brainwave signal acquired from a user (viewer) observing the image and reproduction control information of the image.

A seventh aspect of the present disclosure is a program causing an information processing device to execute information processing, in which the program causes a data processing unit of the information processing device to generate assessment information set to enable identification of whether a brainwave signal is output when a certain image is presented in association with the brainwave signal acquired from a user (viewer) observing the image and reproduction control information of the image.

Note that a program according to the present disclosure is, for example, a program provided in computer-readable format to an information processing device or a computer system capable of executing various program code, the program being providable by a storage medium or communication medium. By providing such a program in a computer-readable format, processing corresponding to the program is realized on the information processing device or the computer system.

Further objectives, features, and advantages of the present disclosure will be clarified by a more detailed description based on the embodiments of the present disclosure described hereinafter and the attached drawings. Note that in this specification, the term "system" refers to a logical aggregate configuration of multiple devices, and the respective devices of the configuration are not limited to being inside the same housing.

Advantageous Effects of Invention

According to an embodiment of the present disclosure, a configuration in which image assessment information is generated on the basis of a brainwave signal of a user observing an image and analysis information of a degree of interest, a region of interest, and the like of the image presented to the user is acquired is realized.

Specifically, for example, a content delivery unit that delivers image content, a data transceiver unit that receives delivery content, a head-mounted display that presents content, and a content analysis unit that analyzes content assessment information are included. The data transceiver unit generates assessment information capable of identifying whether the brainwave signal is output when a certain image is presented in association with image reproduction control information and the brainwave signal acquired from the user and outputs the assessment information to a content analysis device. The content analysis device acquires analysis information such as the degree of interest in the image presented to the user or a region of interest using the brainwave signal.

In this configuration, a configuration in which the image assessment information is generated and analysis information such as the degree of interest in an image presented to the user or a region of interest is acquired on the basis of the brainwave signal of the user observing an image is realized.

Note that the advantageous effects described in this specification are merely for the sake of example and non-limiting, and there may be additional advantageous effects.

MODE(S) FOR CARRYING OUT THE INVENTION

Hereinafter, details of an information processing device, an information processing method, and a program according to the present disclosure will be described with reference to the drawings. Note that the description will be made in accordance with the following sections.
1. Overview of configuration and process of information processing system according to present disclosure
2. Configuration and process of information processing system according to Embodiment 1
3. Configuration and process of information processing system according to Embodiment 2
4. Configuration and process of information processing system according to Embodiment 3
5. Configuration and process of information processing system according to Embodiment 4
6. Configuration and process of information processing system according to Embodiment 5

7. Process to which feedback information is applied (Embodiment 6)
8. Hardware configuration example of information processing device
9. Summary of configuration of present disclosure

[1. Overview of Configuration and Process of Information Processing System According to Present Disclosure]

First, an overview of a configuration and a process of an information processing system according to the present disclosure will be described.

Figure 1:
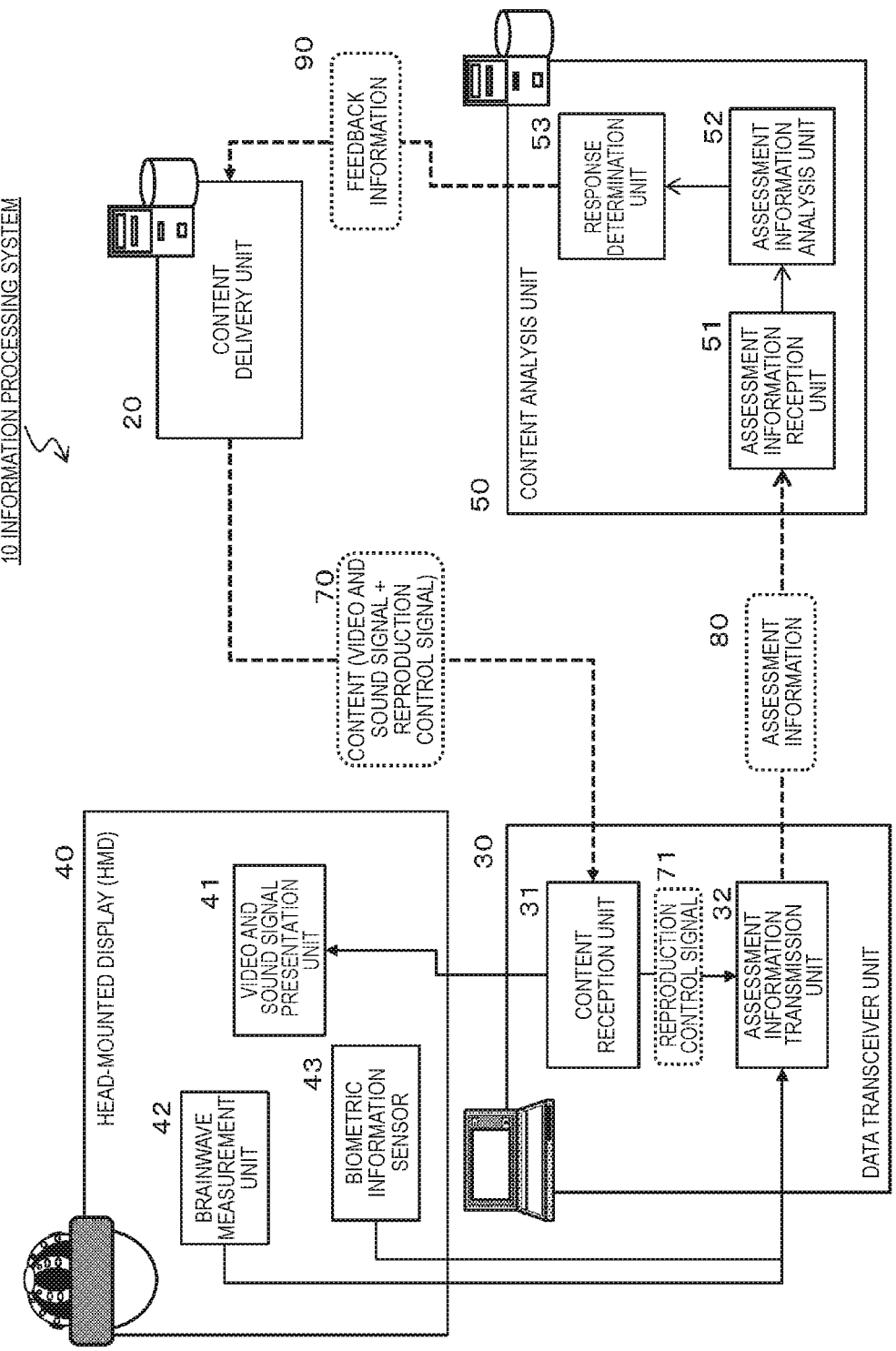
FIG. 1 is an explanatory diagram illustrating a configuration example of an information processing system according to the present disclosure.

FIG. 1 is a diagram illustrating a configuration example of an information processing system 10 according to the present disclosure.

Content 70 configured mainly from a moving image such as video content or game content is delivered from a content delivery unit 20 illustrated in FIG. 1 via a network such as the Internet.

Note that the content 70 includes a reproduction control signal such as a time code serving as reproduction timing information, frame information, or chapter information in addition to video and sound signals which are reproduction data.

The content 70 delivered by the content delivery unit 20 is received by a content reception unit 31 of a data transceiver unit 30 such as a PC on a user (viewer) side.

The received content is output to a video and sound signal presentation unit 41 of a head-mounted display (HMD) 40 of a user (viewer).

The video and sound signal presentation unit 41 is configured as a display (display unit), a speaker, or the like.

In addition, a reproduction control signal 71 such as a time code, frame information, or chapter information is also supplied to an assessment information transmission unit 32.

The head-mounted display (HMD) 40 includes a brainwave measurement unit 42 and a biometric information sensor 43.

The brainwave measurement unit 42 and the biometric information sensor 43 measure brainwaves (electroencephalogram (EEG)) or biometric information of the user appreciating the content 70 and outputs the measured data to the assessment information transmission unit 32 of the data transceiver unit 30.

The assessment information transmission unit 32 of the data transceiver unit 30 transmits the acquired brainwaves and biometric information of the user to the content analysis unit 50 via a network.

Note that the assessment information transmission unit 32 generates and transmits brainwaves or biometric information of the user as brainwaves or biometric information set to enable identification of whether data is data corresponding to a certain image of reproduction content, that is, set as data corresponding to a frame or data corresponding to a reproduction time.

For this correspondence, reproduction control information 71 received from the content delivery server 20 is used as attribute information of the content 70.

The reproduction control information 71 includes information such as a time code which is reproduction time information, frame identification information, and chapter information including a scene change position or the like.

The assessment information transmission unit 32 of the data transceiver unit 30 generates correspondence data set to enable identification of whether data of the brainwaves and the biometric information is data of a certain reproduction time of the content by associating, for example, the time code acquired from the reproduction control information 71 with the brainwaves or the biometric information of the user acquired from the head-mounted display 40 and transmits the correspondence data to the content analysis unit 50.

An assessment information reception unit 51 of the content analysis unit 50 receives the brainwaves or the biometric information of the user transmitted by the data transceiver unit such as a PC which is a user (viewer)-side device and outputs the brainwaves or the biometric information to an assessment information analysis unit 52.

The assessment information analysis unit 52 analyzes whether certain brainwaves or biometric information is output with regard to a certain image of the content 70 on the basis of the brainwaves or the biometric information of the user and analyzes a region of interest (ROI), a degree of interest, assessment, a degree of concentration, a degree of fatigue, and the like of the user with regard to the content.

The analyzed information of the assessment information analysis unit 52 is output to a response determination unit 53.

The response determination unit 53 generates determination data indicating a response of the user to the content 70 presented to the user on the basis of an analysis result in the assessment information analysis unit 52. The determination data can be executed in various data units such as units of data corresponding to the entire content 70, units of chapters, or units of frames.

The determination data generated by the response determination unit 53 can be supplied as feedback information 90 to the content delivery unit 20.

The content delivery unit 20 can execute content control such as a change in the details of the content 70 delivered to the user on the basis of the feedback information 90.

In the system according to the present disclosure, content assessment such as an attraction of the user in the content is configured to be executed using the brainwaves (electroencephalogram (EEG)) of the user (viewer) measured in the brainwave measurement unit.

The measurement of the brainwaves (electroencephalogram (EEG)) is simpler and relatively less expensive than with a near infra-red spectoroscopy (NIRS) that radiates infrared light and analyzes a pattern of its reflected light, and thus cost is considerably suppressed and it can be easily mounted on the HMD.

Hereinafter, configurations and processes of a plurality of specific embodiments will be described in sequence.

[2. Configuration and Process of Information Processing System According to Embodiment 1]

A configuration and a process of the information processing system according to Embodiment 1 will be described with reference to FIG. 2 and the subsequent drawings.

Figure 2:
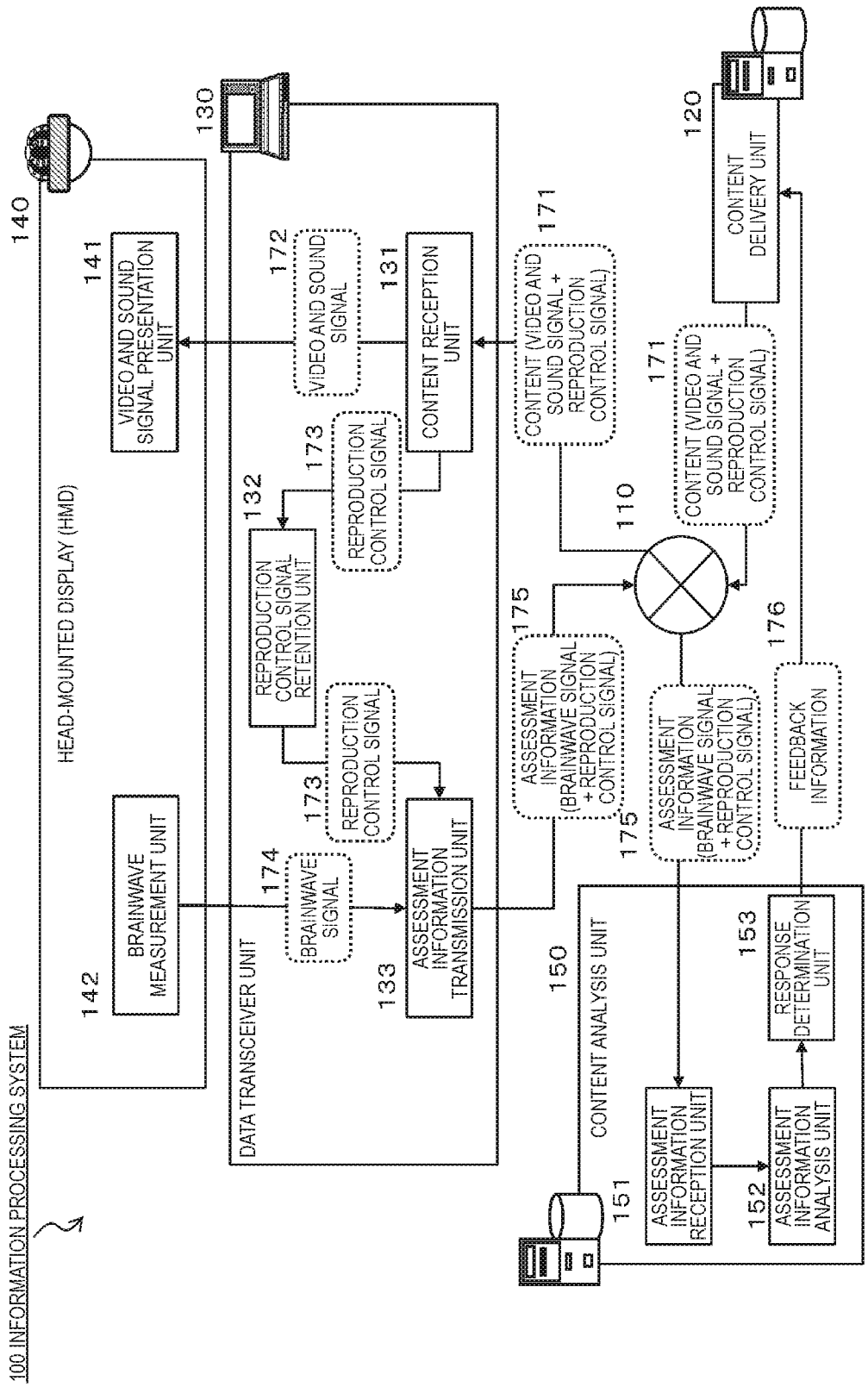
FIG. 2 is an explanatory diagram illustrating a configuration example of an information processing system according to the present disclosure.

FIG. 2 illustrates the following four configurations, as will be described with reference to FIG. 1:
a content delivery unit 120;
a data transceiver unit 130;
a head-mounted display (HMD) 140; and
a content analysis unit 150.

The content delivery unit 120 delivers content (a video and sound signal+a reproduction control signal) 171 via a network 110 such as the Internet to a PC which is a user (viewer)-side device or the data transceiver unit 130 such as a set-top box or a stationary game device connected to the network 110.

The video and sound signal 171 included in the content 171 is transmitted and output from the data transceiver unit 130 to the head-mounted display (HMD) 140.

In addition, a reproduction control signal 173 included in the content 171 is output and maintained in the reproduction control signal retention unit 132.

The reproduction control signal 173 includes information such as a time code which is reproduction time information, frame identification information, and chapter information including a scene change position or the like.

A video and sound signal presentation unit 141 that presents the video and sound signal and a brainwave measurement unit 142 that measures brainwaves of the user are mounted on the head-mounted display (HMD) 140.

The brainwave measurement unit 142 measures a potential change on the scalp of the user (viewer) through electrodes (nodes) worn on the head of the user (viewer).

Disposition of the electrodes (nodes) is standard disposition called International 10-20 system, but distinctive disposition or disposition in which the number of electrodes is limited may be used.

In addition, when the electrodes are worn, a gel or an electrolytic solution for improving conductivity is used in some cases or the electrodes are closely adhered by applying pressure mechanically in some cases. Any method may be used.

Note that when brainwaves are recorded, it is necessary to associate the brainwaves with stimuli (images) when the stimuli are presented. Therefore, information regarding timings of the presentation of the stimuli (images) is recorded along with the brainwaves.

Figure 3:
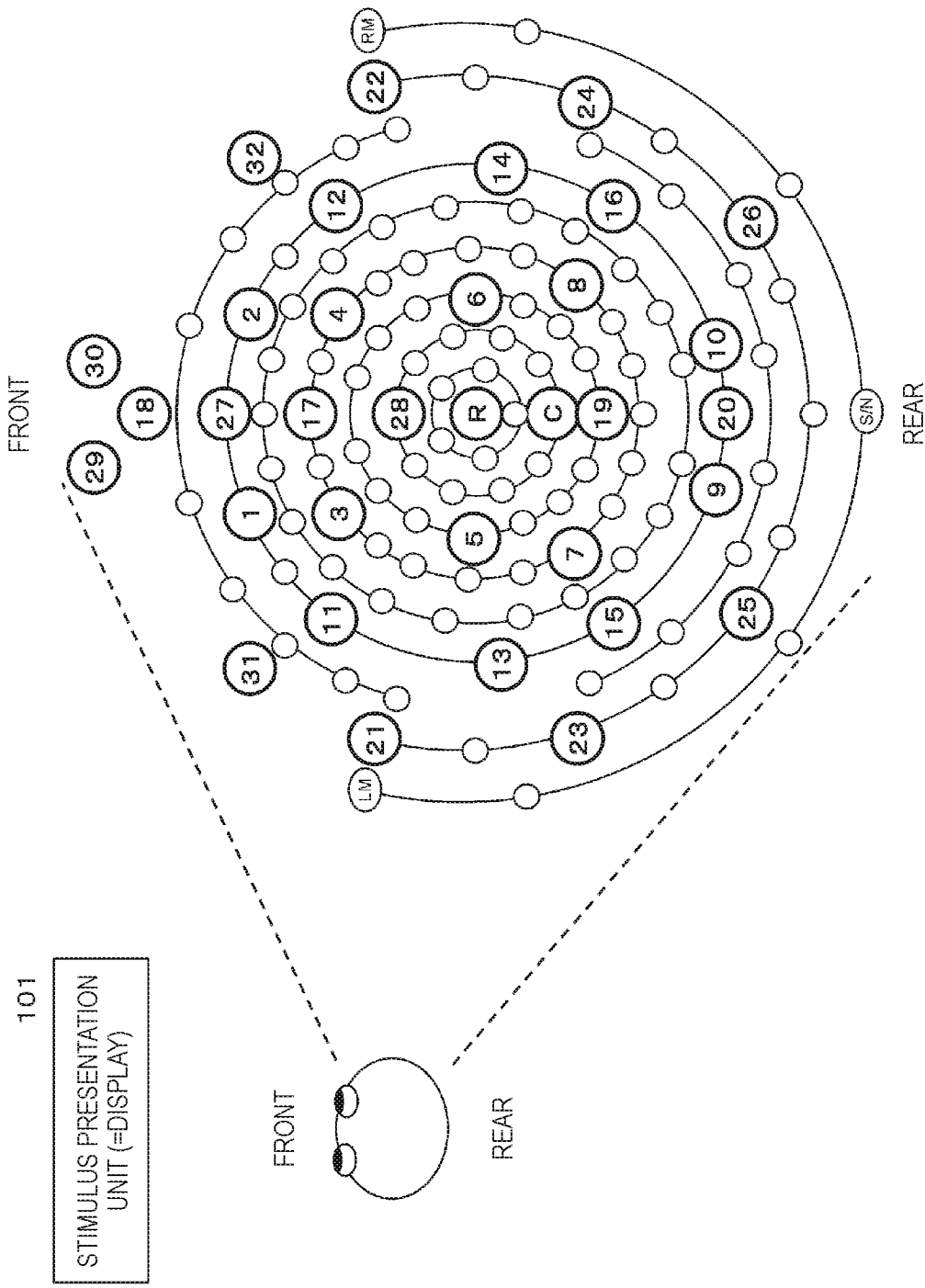
FIG. 3 is an explanatory diagram illustrating a disposition example of electrodes worn on the head of a user (viewer).

An example of disposition of electrodes worn on the head of the user (viewer) is illustrated in FIG. 3.

The upper side of FIG. 3 is a head front side of the user (viewer) and the lower side of FIG. 3 is a head rear side of the user (viewer).

The electrodes are located at 32 positions of 1 to 32 illustrated in FIG. 3.

The head-mounted display (HMD) has a configuration in which a band for fastening the HMD covers a parietal region or an occipital region in many cases. By setting electrodes in the band in addition to a frontal region which is a region on a display unit side of the HMD, it is possible to measure brainwaves of all regions of the head and ascertain changes in the brainwaves more accurately.

In this way, the head-mounted display (HMD) 140 has a configuration in which the brainwave measurement electrodes are set in the regions of the head of the user (viewer) on which the head-mounted display (HMD) 140 is worn.

The brainwave measurement unit 142 measures signals obtained from at least some electrodes among the 32 electrodes illustrated in FIG. 3.

For example, signals obtained from all the 32 electrodes may be used.

Alternatively, only brainwave measurement signals obtained from the electrodes known to measure brainwaves in accordance with visual stimuli, for example, electrode numbers 9, 10, 20, and the like illustrated in FIG. 3 may be configured to be used.

Note that as measurement signals of the brainwave measurement unit 142, brainwave signals in units of electrodes may be used or an integrated component of a plurality of brainwave signals from the plurality of electrodes (weight-added signal or the like) may be used.

The brainwave measurement unit 142 measures brainwaves of the user appreciating the content 171 and outputs a measured brainwave signal 174 to an assessment information transmission unit 133 of the data transceiver unit 130.

The assessment information transmission unit 133 of the data transceiver unit 130 transmits the acquired brainwave signal 174 of the user to the content analysis unit 150 via a network.

Note that the assessment information transmission unit 133 transmits the brainwave signal 174 measured from the user as a brainwave signal set to enable identification of whether data is data corresponding to a certain image of the reproduction content, that is, set as data corresponding to a frame or data corresponding to a reproduction time.

For this correspondence, reproduction control information 173 received from the content delivery server 120 is used as attribute information of the content 171.

The reproduction control signal 173 is information in which a time code which is reproduction time information, frame identification information, chapter information including a scene change position or the like, and the like are recorded.

The assessment information transmission unit 133 of the data transceiver unit 130 generates, for example, assessment information (a brainwave signal+a reproduction control signal) 175 of the user including correspondence data set to enable identification of whether the brainwave signal is data of a certain reproduction time of the content by associating the time code acquired from the reproduction control signal 173 with the brainwave signal 174 of the user acquired from the head-mounted display 140, and transmits the assessment information to the content analysis unit 150.

The assessment information reception unit 151 of the content analysis unit 150 receives the assessment information (the brainwave signal+the reproduction control signal) 175 of the user transmitted by the data transceiver unit such as a PC which is a user (viewer)-side device and outputs the assessment information to the assessment information analysis unit 152.

The assessment information analysis unit 152 analyzes which brainwave signal is output with regard to, for example, a certain image frame of the content 171 on the basis of the brainwaves of the user and analyzes the degree of interest, assessment, the degree of concentration, the degree of fatigue, and the like of the user with regard to the content.

The assessment information analysis unit 152 executes an analysis process focused on a time relation (for example, P300) between presentation of a scene and a change in the brainwaves or a transition response of potential, an analysis process focused on a frequency component (for example, a α wave) included in the brainwaves, or the like.

Note that it is sufficient that which region of the head is used at the time of the analysis of brainwaves is decided in accordance with an assessment item. For example, when a change in lightness in a presented video signal is assessed, a change in brainwaves in an initial visual cortex may be focused on. When an emotion such as pleasure or discomfort caused by a video signal is assessed, a change in brainwaves in a frontal region from a parietal region may be focused on. When a sound signal is assessed, a change in brainwaves in a temporal region may be focused on.

The analyzed information of the assessment information analysis unit 152 is output to a response determination unit 153.

The response determination unit 153 generates determination data indicating a response of the user to the content 171 presented to the user on the basis of an analysis result in the assessment information analysis unit 152. The determination data can be executed in various data units such as units of data corresponding to the entire content 171, units of chapters, or units of frames.

The determination data generated by the response determination unit 153 can be supplied as feedback information 176 to the content delivery unit 210.

The content delivery unit 120 can execute content control such as a change in the details of the content 171 delivered to the user on the basis of the feedback information 176.

[3. Configuration and Process of Information Processing System According to Embodiment 2]

Next, a configuration and a process of the information processing system according to Embodiment 2 will be described with reference to FIG. 4 and the subsequent drawings.

Figure 4:
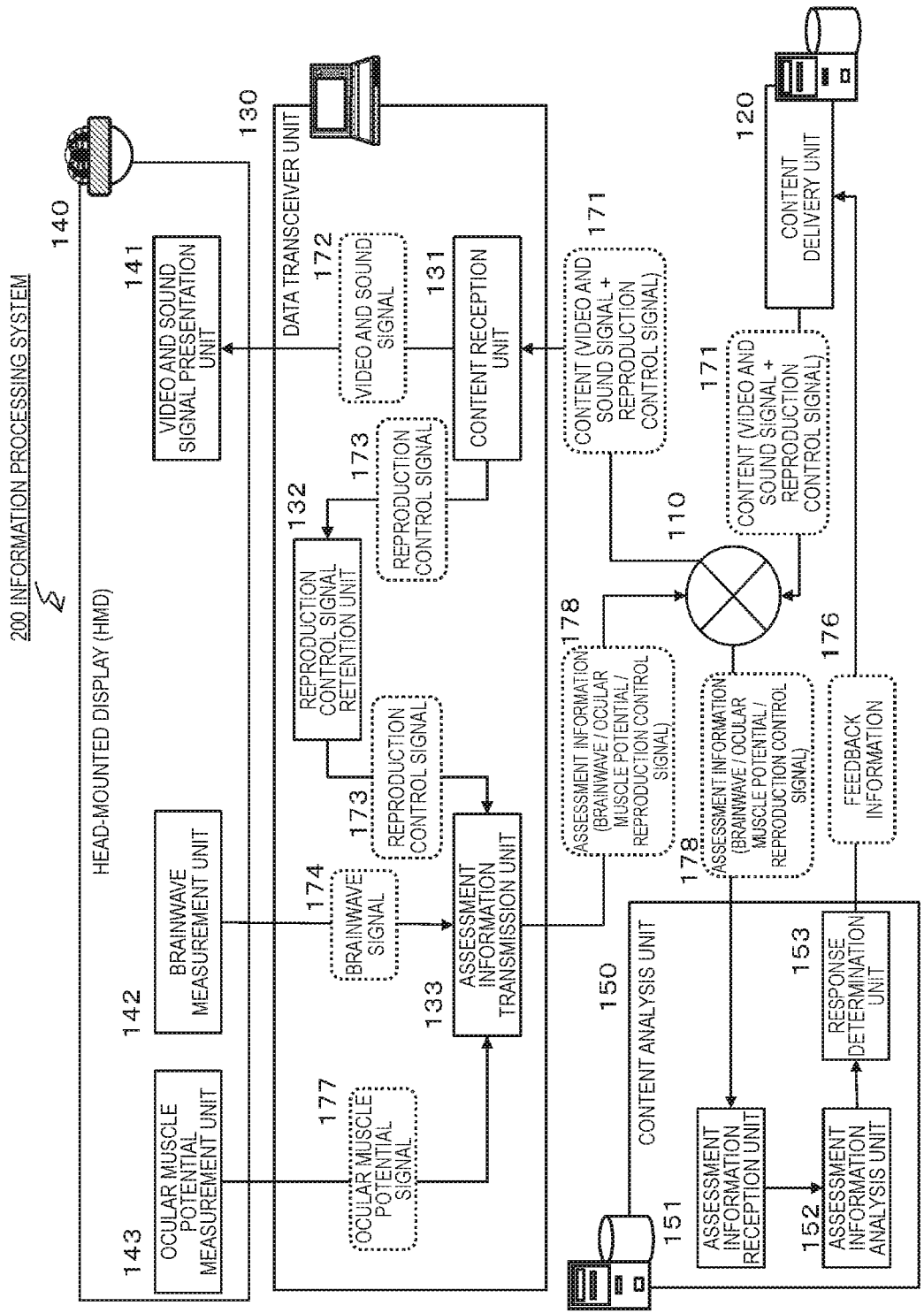
FIG. 4 is an explanatory diagram illustrating a configuration example of an information processing system according to the present disclosure.

A configuration example of an information processing system 200 according to Embodiment 2 is illustrated in FIG. 4.

The information processing system 200 illustrated in FIG. 4 has the following four configurations similar to those of Embodiment 1 described with reference to FIG. 2:

a content delivery unit 120;
a data transceiver unit 130;
a head-mounted display (HMD) 140; and
a content analysis unit 150.

The content delivery unit 120 delivers content (a video and sound signal+a reproduction control signal) 171 via a network 110 such as the Internet to a PC which is a user (viewer)-side device or the data transceiver unit 130 such as a set-top box or a stationary game device connected to the network 110.

The video and sound signal 171 included in the content 171 is transmitted and output from the data transceiver unit 130 to the head-mounted display (HMD) 140.

In addition, a reproduction control signal 173 included in the content 171 is output and maintained in the reproduction control signal retention unit 132.

The reproduction control signal 173 includes information such as a time code which is reproduction time information, frame identification information, and chapter information including a scene change position or the like.

A video and sound signal presentation unit 141 that presents the video and sound signal, a brainwave measurement unit 142 that measures brainwaves of the user, and an ocular muscle potential measurement unit 143 are mounted on the head-mounted display (HMD) 140.

Similar to Embodiment 1 described above, the brainwave measurement unit 142 measures a potential change on the scalp of the user (viewer) through electrodes (nodes) worn on the head of the user (viewer).

For example, the electrode disposition described above with reference to FIG. 3 is provided.

The ocular muscle potential measurement unit 143 is used to analyze a region of interest (ROI) of the user (viewer). Specifically, motions of the eyes generated by motions of muscles (ocular muscles) connected to the eyes are used. The electrodes are disposed near both eyes and an electromyogram occurring due to the motions of the ocular muscles is measured as a change in potential. It is estimated from the change in the potential how much the eyes move and a direction in which the eyes move is each further estimated from a positive or negative change in the potential.

Figure 5:
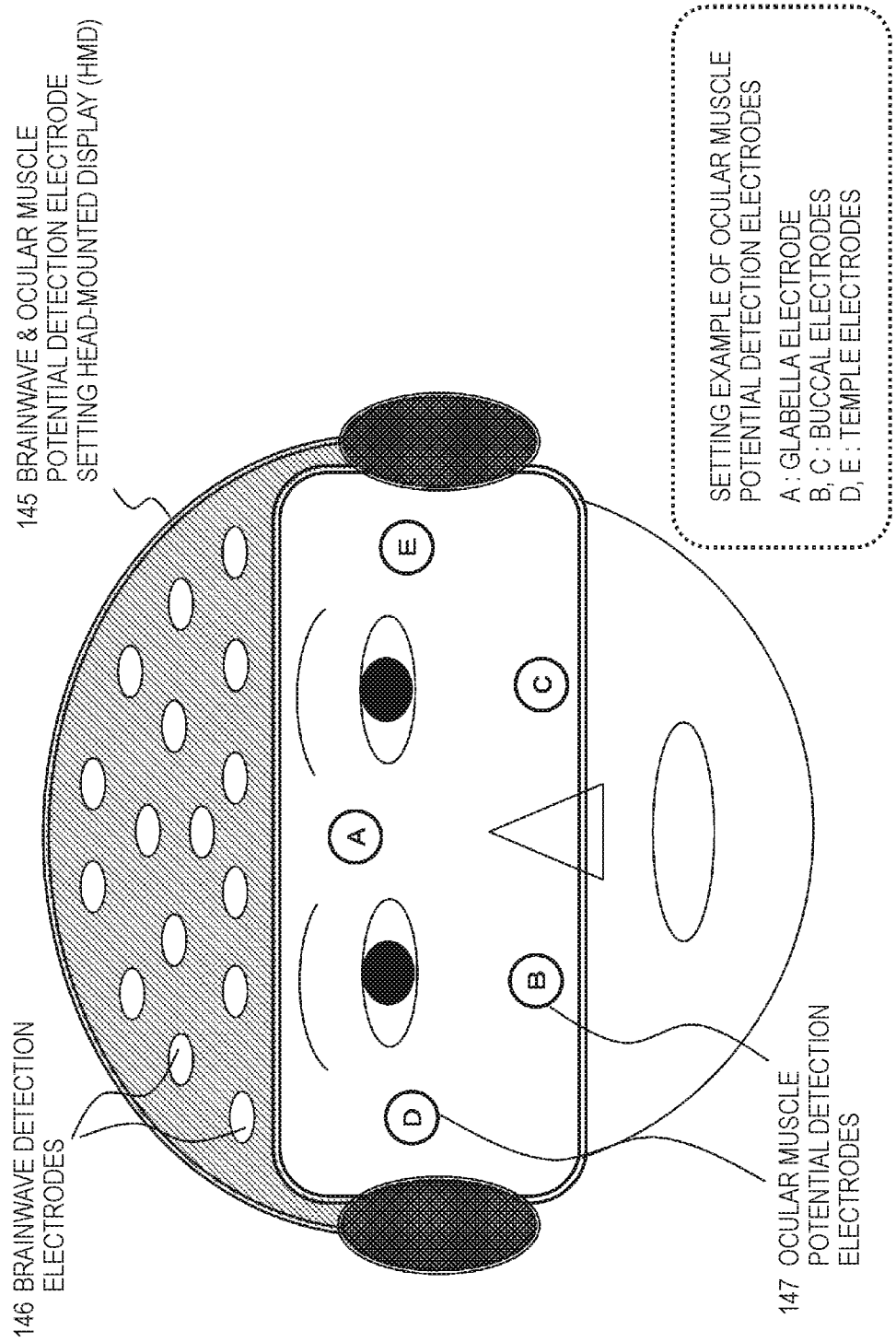
FIG. 5 is an explanatory diagram illustrating a disposition example of the electrodes worn on the front surface of the head of the user (viewer).

A setting example of ocular muscle potential detection electrodes in the ocular muscle potential measurement unit 143 is illustrated in FIG. 5.

FIG. 5 is a diagram illustrating an example of a brainwave & ocular muscle potential detection electrode setting head-mounted display (HMD) 145.

The brainwave & ocular muscle potential detection electrode setting head-mounted display (HMD) 145 includes brainwave detection electrodes 146 and ocular muscle potential detection electrodes 147.

The brainwave detection electrodes 146 have, for example, the electrode disposition described above with reference to FIG. 3.

The ocular muscle potential detection electrodes 147 are set in a front side region of the face which is a display unit side of the head-mounted display (HMD), as illustrated in FIG. 5. As illustrated in the drawing, a glabella electrode A, buccal electrodes B and C, temple electrodes D and E, and the like are included.

As illustrated in FIG. 5, the head-mounted display (HMD) 140 includes the ocular muscle potential measurement electrodes in the region of the face of the user (viewer) of the head-mounted display (HMD) 140.

The ocular muscle potential detection electrodes 147 (the electrodes A to E) illustrated in FIG. 5 are set at ocular muscle positions to detect motions of the muscles (ocular muscles) connected to the eyes of the user (viewer).

At the electrode positions, an electromyogram potential is changed by motions of the ocular muscles. How much the eyes move is estimated from the change amount of the potential and a direction in which the eyes move is further estimated from a positive or negative change of the potential.

Note that precision of a region-of-interest estimation result obtained using the ocular muscle potential detection electrodes 147 (the electrodes A to E) is less than that of a dedicated device that detects pupils using infrared light and measures motions of eyeballs. However, it is possible to guarantee precision to the extent that a certain viewed region of a screen is estimated.

Referring back to FIG. 4, the configuration and the process of the information processing system 200 according to Embodiment 2 will be continuously described.

The brainwave measurement unit 142 and the ocular muscle potential measurement unit 143 of the head-mounted display (HMD) 140 measure a brainwave and an ocular muscle potential of the user appreciating the content 171 and outputs a measured brainwave signal 174 and ocular muscle potential signal 177 to the assessment information transmission unit 133 of the data transceiver unit 130.

The assessment information transmission unit 133 of the data transceiver unit 130 transmits the acquired brainwave signal 174 and ocular muscle potential signal 177 of the user to the content analysis unit 150 via a network.

Note that the assessment information transmission unit 133 transmits the brainwave signal 174 and the ocular muscle potential signal 177 measured from the user as data set to be able to identify whether data is data corresponding to a certain image of the reproduction content, that is, set as data corresponding to a frame or data corresponding to a reproduction time.

For this correspondence, reproduction control information 171 received from the content delivery server 120 is used as attribute information of the content 170.

The reproduction control signal 173 is information in which a time code which is reproduction time information, frame identification information, chapter information including a scene change position or the like, and the like are recorded.

The assessment information transmission unit 133 of the data transceiver unit 130 generates, for example, assessment information (a brainwave signal+ocular muscle potential signal+a reproduction control signal) 178 of the user including correspondence data set to enable identification of whether the brainwave signal or electromyogram potential signal is data of a certain reproduction time of the content by associating the time code acquired from the reproduction control signal 173 with the brainwave signal 174 and the ocular muscle potential signal 177 of the user acquired from the head-mounted display 140, and transmits the assessment information to the content analysis unit 150.

The content analysis unit 150 according to Embodiment 2 generates content assessment information based on a brainwave and analyzes a region of interest of the user (viewer) on the basis of an ocular muscle potential signal as in Embodiment 1 described above. Note that in the analysis of the region of interest, not only the ocular muscle potential signal but also a brainwave signal may be used.

Figure 6:
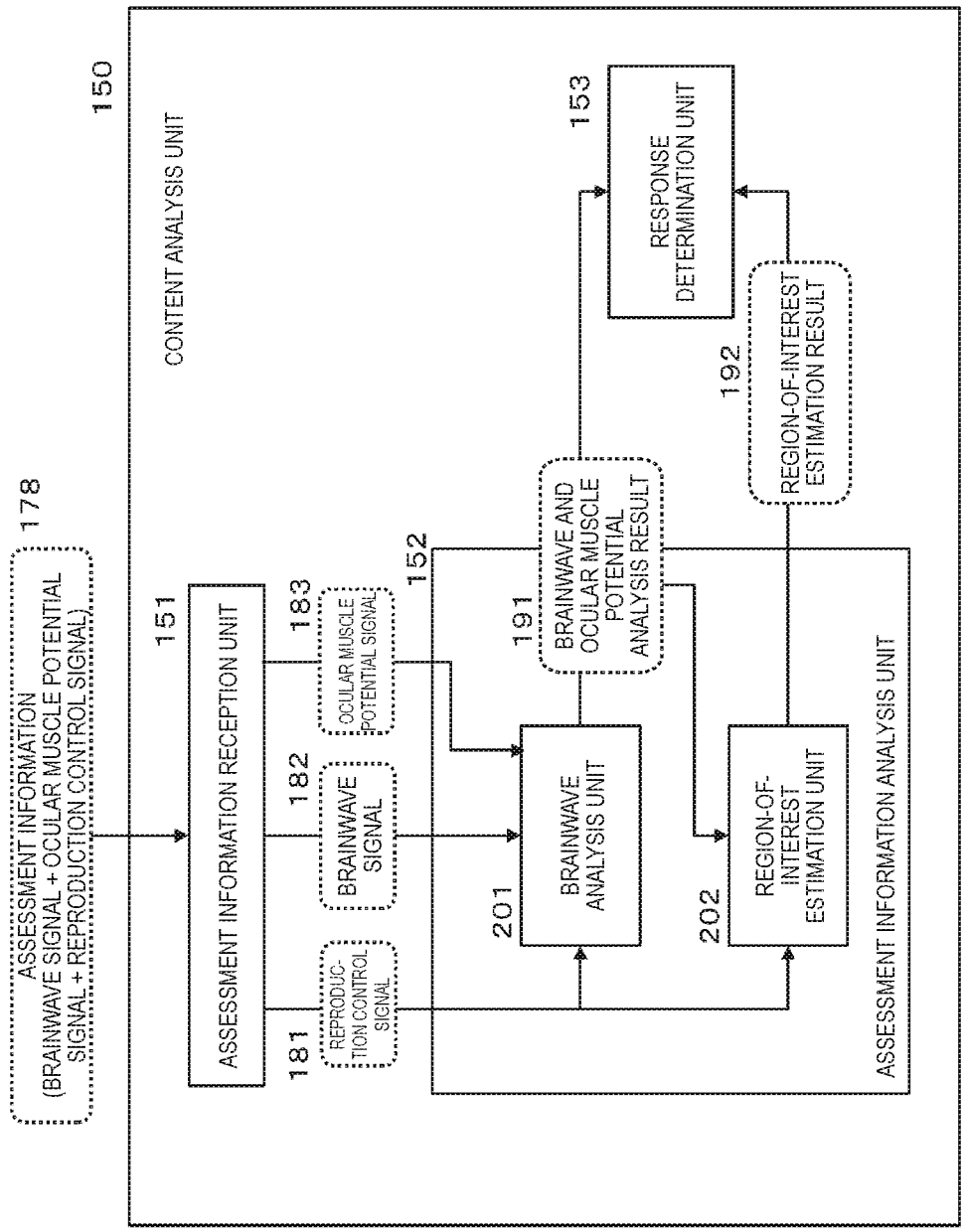
FIG. 6 is an explanatory diagram illustrating a configuration and a process of a content analysis unit.

A detailed configuration of the content analysis unit 150 according to Embodiment 2 is illustrated in FIG. 6.

The assessment information reception unit 151 of the content analysis unit 150 receives the assessment information (the brainwave signal+ocular muscle potential signal+ the reproduction control signal) 178 of the user transmitted by the data transceiver unit 130 such as a PC which is a user (viewer)-side device and outputs the assessment information to the assessment information analysis unit 152.

As illustrated in FIG. 6, a reproduction control signal 181, a brainwave signal 182, and an ocular muscle potential signal 183 are input from the assessment information reception unit 151 of the content analysis unit 150 to the assessment information analysis unit 152.

The assessment information analysis unit 152 includes a brainwave analysis unit 201 and a region-of-interest estimation unit 202.

The brainwave analysis unit 201 inputs the reproduction control signal 181, the brainwave signal 182, and the ocular muscle potential signal 183, generates, for example, a brainwave and ocular muscle potential analysis result 191 including a brainwave signal in units of image frames, and outputs the brainwave and ocular muscle potential analysis result 191 to the region-of-interest estimation unit 202 and the response determination unit 153.

The region-of-interest estimation unit 202 inputs the reproduction control signal 181 and the brainwave and ocular muscle potential analysis result 191 output from the brainwave analysis unit 201, estimates an eyeball motion of the user (viewer) corresponding to each image frame, and estimates whether the user (viewer) actually views a certain image region of each presented image frame.

That is, a region of interest of the user in each image frame is analyzed and a region-of-interest estimation result 192 is generated and output to the response determination unit 153.

The region-of-interest estimation unit 202 analyzes a change in the brainwave at a reproduction time of each image frame in association with the time code included in the reproduction control signal 181, that is, the time code which is reproduction time information of each image frame, and the brainwave and ocular muscle potential analysis result 191, estimates how the eyeballs move, and generates region-of-interest information indicating a certain image region of each image frame in which the user (viewer) is interested.

As described above, it is possible to estimate both a motion direction and a motion amount of the eyes in accordance with the ocular muscle potential. From the data, the region-of-interest estimation unit 202 generates region-of-interest information indicating a certain image region of each image frame in which the user (viewer) is interested. Note that the degree of interest in the region of interest may be configured to be estimated further with reference to the brainwave signal to calculate an interest level (the extent of the interest in an image of the region of interest) of the user (viewer).

Note that, in Embodiment 2, similar to Embodiment 1, the assessment information analysis unit 152 executes an analysis process focused on a time relation (for example, P300) between presentation of a scene and a change in the brainwaves or a transition response of potential, an analysis process focused on a frequency component (for example, a α wave) included in the brainwaves, or the like.

Note that it is sufficient if which region of the head is used at the time of the analysis of brainwaves is decided in accordance with an assessment item. For example, when a change in lightness in a presented video signal is assessed, a change in brainwaves in an initial visual cortex may be focused on. When an emotion such as pleasure or discomfort caused by a video signal is assessed, a change in brainwaves in a frontal region from a parietal region may be focused on. When a sound signal is assessed, a change in brainwaves in a temporal region may be focused on.

The assessment information analysis unit 152 outputs the brainwave and ocular muscle potential analysis result 191 and the region-of-interest estimation result 192 as analysis information to the response determination unit 153.

The response determination unit 153 generates determination data indicating a response of the user to the content 171 presented to the user on the basis of an analysis result in the assessment information analysis unit 152. The determination data can be executed in various data units such as units of data corresponding to the entire content 171, units of chapters, or units of frames.

The determination data generated by the response determination unit 153 can be supplied as feedback information 176 to the content delivery unit 210.

The content delivery unit 120 can execute content control such as a change in the details of the content 171 delivered to the user on the basis of the feedback information 176.

[4. Configuration and Process of Information Processing System According to Embodiment 3]

Next, a configuration and a process of the information processing system according to Embodiment 3 will be described with reference to FIG. 7.

Figure 7:
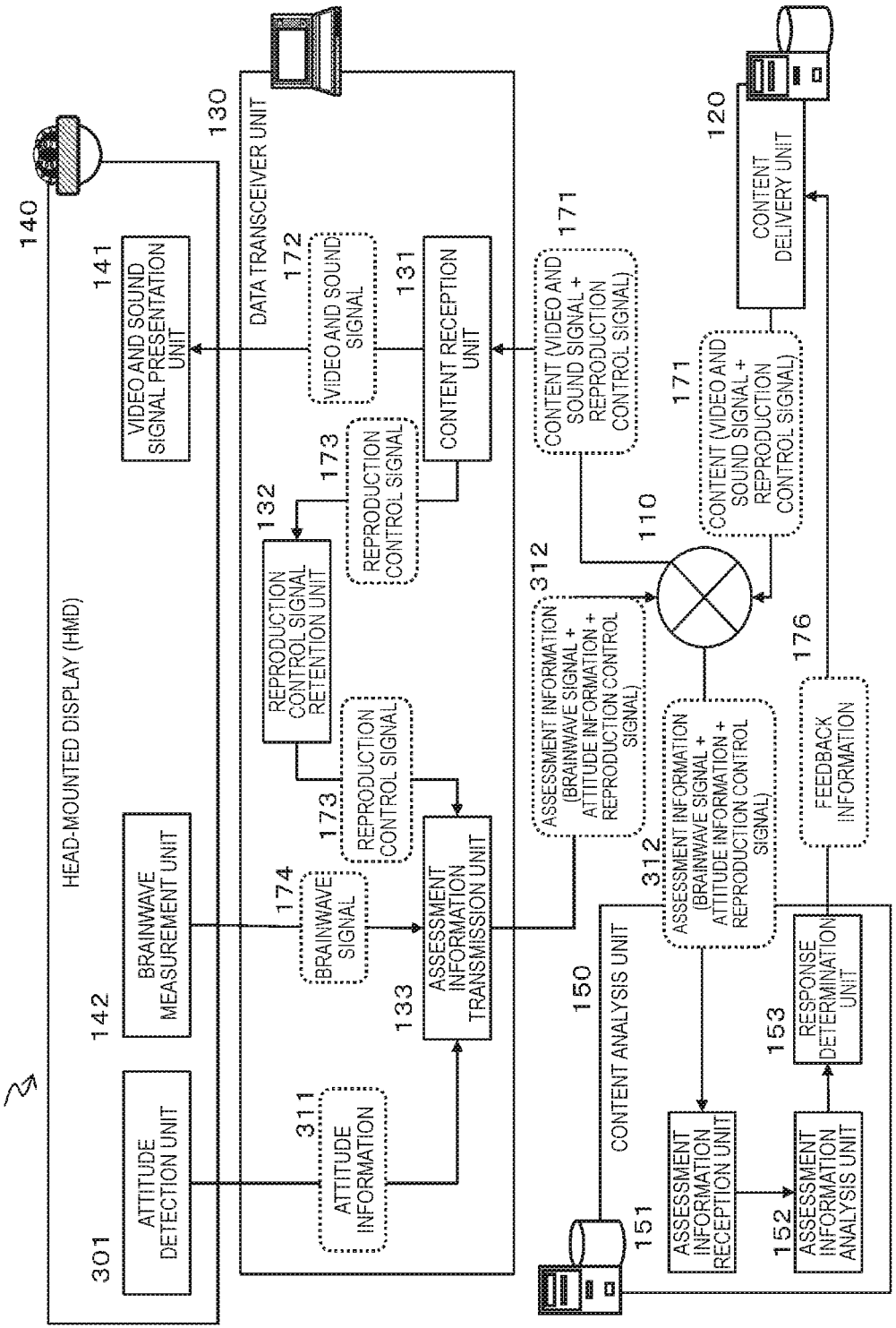
FIG. 7 is an explanatory diagram illustrating a configuration example of an information processing system according to the present disclosure.

A configuration example of an information processing system 300 according to Embodiment 3 is illustrated in FIG. 7.

The information processing system 300 illustrated in FIG. 7 has the following four configurations similar to those of Embodiment 1 described with reference to FIG. 2:

a content delivery unit 120;
a data transceiver unit 130;
a head-mounted display (HMD) 140; and
a content analysis unit 150.

Embodiment 3 provides a configuration in which an attitude detection unit 301 is added to the head-mounted display 140 of the information processing system 100 according to Embodiment 1 described above with reference to FIG. 2.

The attitude detection unit 301 includes, for example, a sensor such as an acceleration sensor or a gyro sensor and has a function of detecting a motion or a change in an attitude of the user (viewer).

An electromyogram occurring due to a motion or a change in an attitude of the user is superimposed as a noise signal on a brainwave measured by the brainwave measurement unit 142 in some cases.

On the basis of the motion or the change in the attitude of the user (viewer) detected by the attitude detection unit 301, an electromyogram (EMG) signal which is a noise component in a brainwave signal is estimated.

The estimation result is used to remove the noise component (the electromyogram signal) from the brainwave signal measured by the brainwave measurement unit 142, and a highly precise brainwave signal is acquired to realize analysis.

A difference between Embodiment 3 and Embodiment 1 is that the head-mounted display 140 includes the attitude detection unit 301. A process in the added configuration will be described.

The attitude detection unit 301 of the head-mounted display 140 includes, for example, a sensor such as an acceleration sensor or a gyro sensor and detects a motion or a change in an attitude of the user (viewer), as described above. The detected signal is attitude information 311 illustrated in FIG. 7.

The brainwave measurement unit 142 and the attitude detection unit 301 of the head-mounted display (HMD) 140 detect a brainwave and an attitude of the user appreciating the content 171 and output the measured brainwave signal 174 and attitude information 311 to the assessment information transmission unit 133 of the data transceiver unit 130.

The assessment information transmission unit 133 of the data transceiver unit 130 transmits the acquired brainwave signal 174 and attitude information 311 of the user to the content analysis unit 150 via a network.

Note that the assessment information transmission unit 133 transmits the brainwave signal 174 and the attitude information 311 measured from the user as data set to be able to identify whether data is data corresponding to a certain image of the reproduction content, that is, set as data corresponding to a frame or data corresponding to a reproduction time.

For this correspondence, reproduction control information 171 received from the content delivery server 120 is used as attribute information of the content 170.

The reproduction control signal 173 is information in which a time code which is reproduction time information, frame identification information, chapter information including a scene change position or the like, and the like are recorded.

The assessment information transmission unit 133 of the data transceiver unit 130 generates, for example, assessment information (a brainwave signal+attitude information+a reproduction control signal) 312 of the user including correspondence data set to enable identification of whether the brainwave signal or attitude information is data of a certain reproduction time of the content by associating the time code acquired from the reproduction control signal 173 with the brainwave signal 174 and the attitude information 311 of the user acquired from the head-mounted display 140, and transmits the assessment information to the content analysis unit 150.

The content analysis unit 150 in Embodiment 3 generates content assessment information based on the brainwave as in Embodiment 1 described above, but estimates an electromyogram (EMG) signal occurring due to a motion or a change in the attitude of the user using the attitude information in this process, removes the electromyogram signal superimposed as the noise signal on the brainwave measured by the brainwave measurement unit 142, and generates a highly precise brainwave signal to execute content analysis.

As described above, the electromyogram signal is superimposed as the noise signal on the brainwave measured by the brainwave measurement unit 142.

The assessment information reception unit 151 of the content analysis unit 150 receives the assessment information (the brainwave signal+the attitude information+the reproduction control signal) 312 of the user transmitted by the data transceiver unit such as a PC which is a user (viewer)-side device and outputs the assessment information to the assessment information analysis unit 152.

The assessment information analysis unit 152 first executes a process of estimating the electromyogram (EMG) signal occurring due to the motion or the change in the attitude of the user using the attitude information and removing the electromyogram signal superimposed as the noise signal on the brainwave measured by the brainwave measurement unit 142.

Next, whether a certain brainwave signal is output with regard to a certain image portion of, for example, the content 171 is analyzed on the basis of the brainwave signal from which the noise is removed, and the degree of interest, assessment, the degree of concentration, the degree of fatigue, and the like of the user with regard to the content are analyzed.

The assessment information analysis unit 152 executes an analysis process focused on a time relation (for example, P300) between presentation of a scene and a change in the brainwaves or a transition response of potential, an analysis process focused on a frequency component (for example, a α wave) included in the brainwaves, or the like.

Note that it is sufficient if which region of the head is used at the time of the analysis of brainwaves is decided in accordance with an assessment item. For example, when a change in lightness in a presented video signal is assessed, a change in brainwaves in an initial visual cortex may be focused on. When an emotion such as pleasure or discomfort caused by a video signal is assessed, a change in brainwaves in a frontal region from a parietal region may be focused on. When a sound signal is assessed, a change in brainwaves in a temporal region may be focused on.

The analyzed information of the assessment information analysis unit 152 is output to a response determination unit 153.

The response determination unit 153 generates determination data indicating a response of the user to the content 171 presented to the user on the basis of an analysis result in the assessment information analysis unit 152. The determination data can be executed in various data units such as units of data corresponding to the entire content 171, units of chapters, or units of frames.

The determination data generated by the response determination unit 153 can be supplied as feedback information 176 to the content delivery unit 210.

The content delivery unit 120 can execute content control such as a change in the details of the content 171 delivered to the user on the basis of the feedback information 176.

[5. Configuration and Process of Information Processing System According to Embodiment 4]

Next, a configuration and a process of the information processing system according to Embodiment 4 will be described with reference to FIG. 8 and the subsequent drawings.

Figure 8:
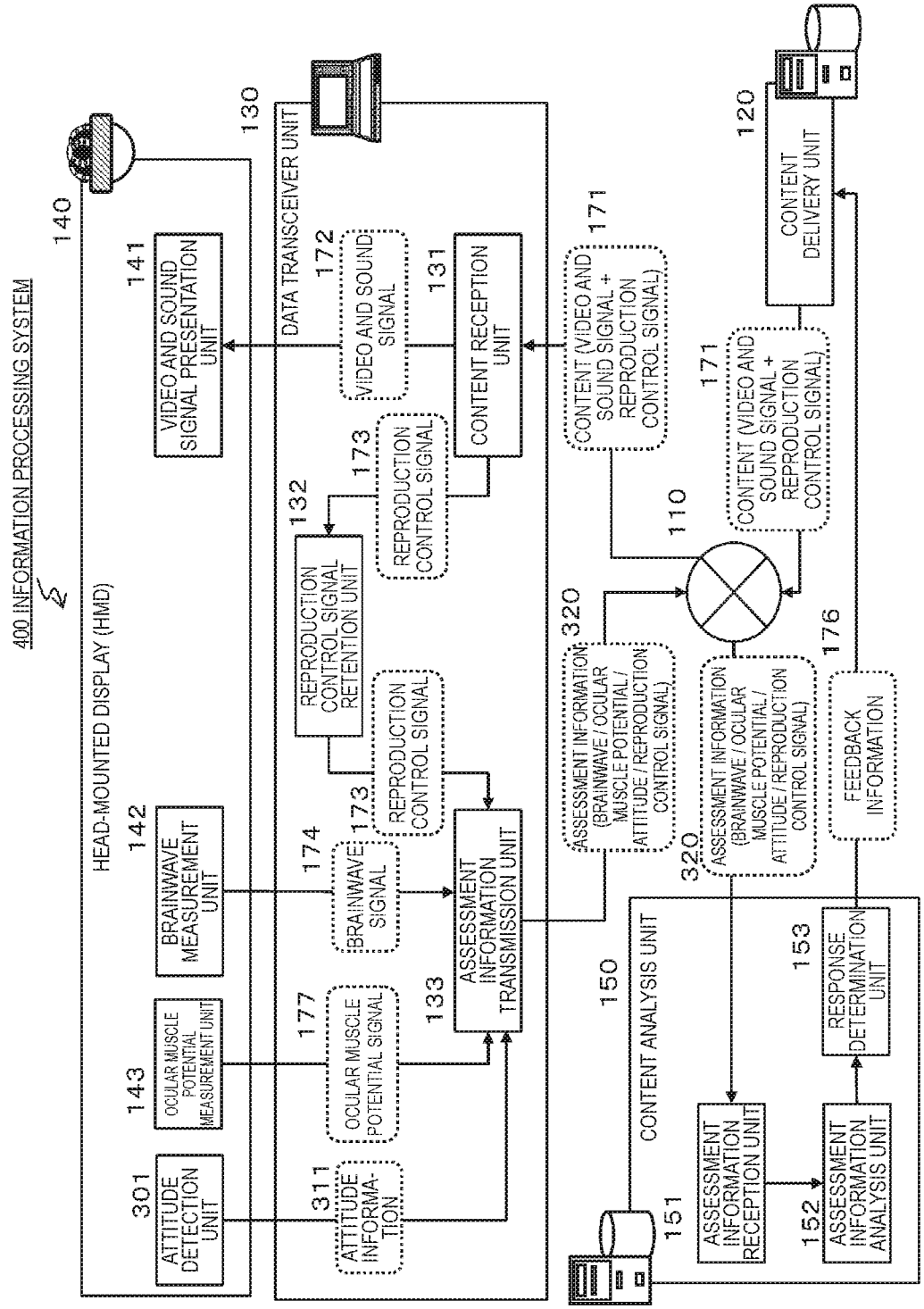
FIG. 8 is an explanatory diagram illustrating a configuration example of an information processing system according to the present disclosure.

A configuration example of an information processing system 400 according to Embodiment 4 is illustrated in FIG. 8.

The information processing system 400 illustrated in FIG. 8 has the following four configurations similar to those of Embodiment 1 described with reference to FIG. 2:
  a content delivery unit 120;
  a data transceiver unit 130;

a head-mounted display (HMD) 140; and a content analysis unit 150.

The head-mounted display (HMD) 140 according to Embodiment 4 includes not only the video and sound signal presentation unit 141 but also the brainwave measurement unit 142, the ocular muscle potential measurement unit 143, and the attitude detection unit 301.

The ocular muscle potential measurement unit 143 executes the same process as the ocular muscle potential measurement unit 143 in the information processing system 200 according to Embodiment 2 described above with reference to FIGS. 4 to 6. The attitude detection unit 301 executes the same process as the attitude detection unit 301 in the information processing system 300 according to Embodiment 3 described above with reference to FIG. 7.

The ocular muscle potential measurement unit 143 measures an electromyogram occurring due to a motion of an ocular muscle as a change in potential. How much the eyes move can be estimated from the change amount of the potential and a direction in which the eyes move is further estimated from a positive or negative change of the potential.

The attitude detection unit 301 includes, for example, a sensor such as an acceleration sensor or a gyro sensor and has a function of detecting a motion or a change in an attitude of the user (viewer).

The embodiment provides a configuration in which the functions of Embodiment 2 and Embodiment 3 described above are combined.

That is, the embodiment provides a configuration capable of executing processes of analyzing a point of interest on the basis of the ocular muscle potential signal 177 which is a signal measured by the ocular muscle potential measurement unit 143 and removing an electromyogram (EMG) signal included as a noise signal in a brainwave measured by the brainwave measurement unit 142 on the basis of the attitude information 311 which is detection information of the attitude detection unit 301 to acquire a highly precise brainwave signal.

The brainwave measurement unit 142, the ocular muscle potential measurement unit 143, and the attitude detection unit 301 of the head-mounted display 140 illustrated in FIG. 8 detect a brainwave, an ocular muscle potential, and an attitude of the user appreciating the content 171 and output the measured brainwave signal 174, ocular muscle potential signal 177, and attitude information 311 to the assessment information transmission unit 133 of the data transceiver unit 130.

The assessment information transmission unit 133 of the data transceiver unit 130 transmits the acquired brainwave signal 174, ocular muscle potential signal 177, and attitude information 311 of the user to the content analysis unit 150 via a network.

Note that the assessment information transmission unit 133 transmits the brainwave signal 174, the ocular muscle potential signal 177, and the attitude information 311 measured from the user as data set to be able to identify whether data is data corresponding to a certain image of the reproduction content, that is, set as data corresponding to a frame or data corresponding to a reproduction time.

For this correspondence, reproduction control information 171 received from the content delivery server 120 is used as attribute information of the content 170.

The reproduction control signal 173 is information in which a time code which is reproduction time information, frame identification information, chapter information including a scene change position or the like, and the like are recorded.

The assessment information transmission unit 133 of the data transceiver unit 130 generates, for example, assessment information (a brainwave signal+an ocular muscle potential signal+attitude information+a reproduction control signal) 320 of the user including correspondence data set to enable identification of whether the brainwave signal or attitude information is data of a certain reproduction time of the content by associating the time code acquired from the reproduction control signal 173 with the brainwave signal 174, the ocular muscle potential signal 177, and the attitude information 311 of the user acquired from the head-mounted display 140, and transmits the assessment information to the content analysis unit 150.

The content analysis unit 150 according to Embodiment 4 generates content assessment information based on a brainwave and analyzes a region of interest of the user (viewer) on the basis of an ocular muscle potential signal as in Embodiment 1 described above. Note that in the analysis of the region of interest, not only the ocular muscle potential signal but also a brainwave signal may be used.

Furthermore, the content analysis unit 150 in Embodiment 4 estimates an electromyogram (EMG) signal occurring due to a motion or a change in the attitude of the user using the attitude information in this process, removes the electromyogram signal superimposed as the noise signal on the brainwave measured by the brainwave measurement unit 142, and generates a highly precise brainwave signal to execute content analysis.

As described above, the electromyogram signal is superimposed as the noise signal on the brainwave measured by the brainwave measurement unit 142.

Figure 9:
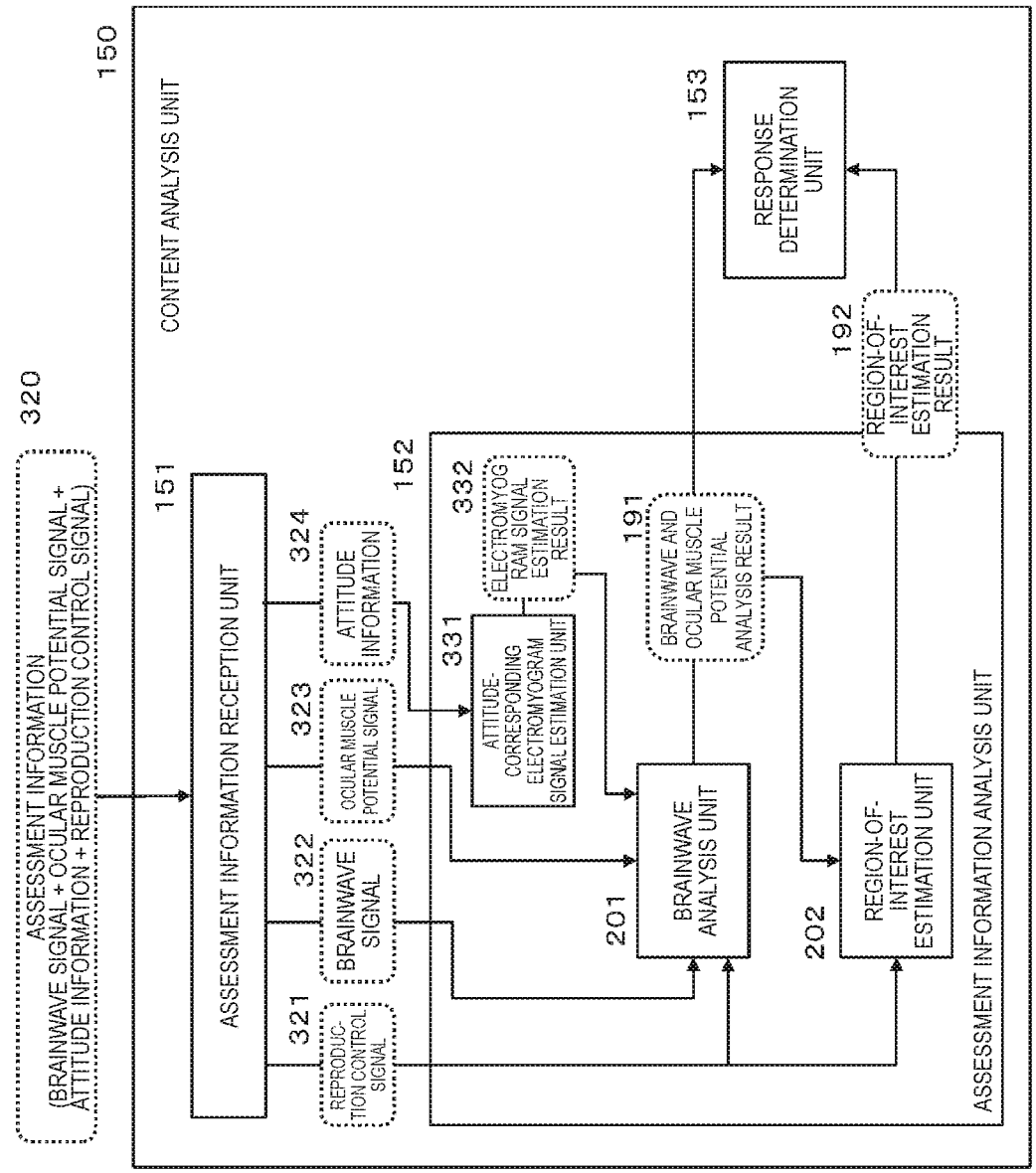
FIG. 9 is an explanatory diagram illustrating a configuration and a process of the content analysis unit.

A detailed configuration of the content analysis unit 150 according to Embodiment 4 is illustrated in FIG. 9.

The assessment information reception unit 151 of the content analysis unit 150 receives the assessment information (the brainwave signal+the ocular muscle potential signal+the attitude information+the reproduction control signal) 320 of the user transmitted by the data transceiver unit 130 such as a PC which is a user (viewer)-side device and outputs the assessment information to the assessment information analysis unit 152.

As illustrated in FIG. 9, a reproduction control signal 321, a brainwave signal 322, an electromyogram potential signal 323, and attitude information 324 are input from the assessment information reception unit 151 of the content analysis unit 150 to the assessment information analysis unit 152.

The assessment information analysis unit 152 includes the brainwave analysis unit 201 and the region-of-interest estimation unit 202 and further includes an attitude-corresponding electromyogram signal estimation unit 331.

The attitude-corresponding electromyogram signal estimation unit 331 estimates an electromyogram (EMG) signal occurring due to a motion or a change in an attitude of the user using the attitude information, generates an electromyogram signal estimation result 332, and outputs the electromyogram signal estimation result 332 to the brainwave analysis unit 201.

The brainwave analysis unit 201 inputs the reproduction control signal 321, the brainwave signal 322, and the electromyogram signal estimation result 332 and first executes a process of removing the electromyogram signal estimation result 332 estimated to be superimposed as a noise signal on the brainwave signal 322 measured by the brainwave measurement unit 142.

Subsequently, whether a certain brainwave signal is output with regard to a certain image portion of, for example, the content 171 is analyzed on the basis of the brainwave signal from which the noise is removed and, for example, the brainwave and ocular muscle potential analysis result 191 including a brainwave signal in units of image frames is generated and output to the region-of-interest estimation unit 202 and the response determination unit 153.

The region-of-interest estimation unit 202 inputs the reproduction control signal 321 and the brainwave and ocular muscle potential analysis result 191 output from the brainwave analysis unit 201, estimates an eyeball motion of the user (viewer) corresponding to each image frame, and estimates whether the user (viewer) actually views a certain image region of each presented image frame.

That is, a region of interest of the user in each image frame is analyzed and a region-of-interest estimation result 192 is generated and output to the response determination unit 153.

The region-of-interest estimation unit 202, for example, analyzes a change in the brainwave at a reproduction time of each image frame in association with the time code included in the reproduction control signal 321, that is, the time code which is reproduction time information of each image frame, and the brainwave and ocular muscle potential analysis result 191, estimates how the eyeballs move, and generates region-of-interest information indicating a certain image region of each image frame in which the user (viewer) is interested.

As described above, it is possible to estimate both a motion direction and a motion amount of the eyes in accordance with the ocular muscle potential. From the data, the region-of-interest estimation unit 202 generates region-of-interest information indicating a certain image region of each image frame in which the user (viewer) is interested. Note that the degree of interest in the region of interest may be configured to be estimated further with reference to the brainwave signal to calculate an interest level (the extent of the interest in an image of the region of interest) of the user (viewer).

Note that, in Embodiment 4, similar to Embodiment 1, the assessment information analysis unit 152 executes an analysis process focused on a time relation (for example, P300) between presentation of a scene and a change in the brainwaves or a transition response of potential, an analysis process focused on a frequency component (for example, a α wave) included in the brainwaves, or the like.

Note that it is sufficient if which region of the head is used at the time of the analysis of brainwaves is decided in accordance with an assessment item. For example, when a change in lightness in a presented video signal is assessed, a change in brainwaves in an initial visual cortex may be focused on. When an emotion such as pleasure or discomfort caused by a video signal is assessed, a change in brainwaves in a frontal region from a parietal region may be focused on. When a sound signal is assessed, a change in brainwaves in a temporal region may be focused on.

The assessment information analysis unit 152 outputs the brainwave and ocular muscle potential analysis result 191 and the region-of-interest estimation result 192 as analysis information to the response determination unit 153.

The response determination unit 153 generates determination data indicating a response of the content 171 presented to the user on the basis of an analysis result in the assessment information analysis unit 152. The determination data can be executed in various data units such as units of data corresponding to the entire content 171, units of chapters, or units of frames.

The determination data generated by the response determination unit 153 can be supplied as feedback information 176 to the content delivery unit 210.

The content delivery unit 120 can execute content control such as a change in the details of the content 171 delivered to the user on the basis of the feedback information 176.

[6. Configuration and Process of Information Processing System According to Embodiment 5]

Next, a configuration and a process of the information processing system according to Embodiment 5 will be described with reference to FIG. 10.

Figure 10:
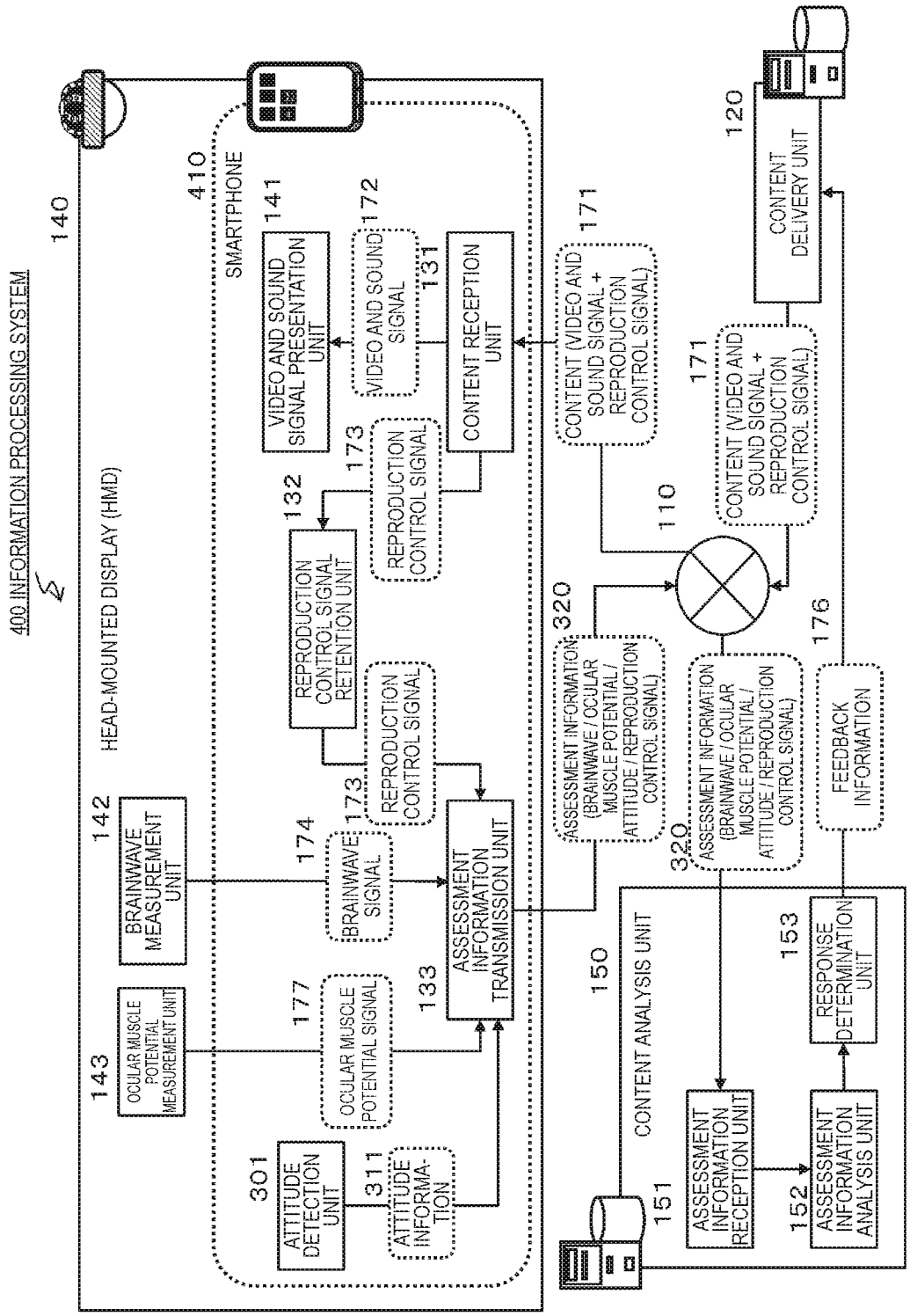
FIG. 10 is an explanatory diagram illustrating a configuration example of an information processing system according to the present disclosure.

Embodiment 5 is set to configure most of the head-mounted display 140 using a smartphone which has recently been widespread, as illustrated in FIG. 10.

That is, a display unit of a smartphone 410 is used as the display unit of the head-mounted display 140.

As illustrated in FIG. 10, the head-mounted display 140 includes the brainwave measurement unit 142 and the ocular muscle potential measurement unit 143.

The smartphone 410 includes not only the content reception unit 131 and the video signal presentation unit 141 but also the reproduction control signal retention unit 132, the assessment information transmission unit 133, and the attitude detection unit 301.

Note that the constituent units are the same as the constituent units described in Embodiment 1 to Embodiment 4 described above.

A general smartphone has a communication function such as LTE or Wi-Fi and includes the content reception unit 131 that receives the content 171 or the assessment information transmission unit 133 that transmits assessment information using the communication function such as LTE or Wi-Fi.

In addition, a general smartphone includes an internal memory and can use the internal memory as the control signal retention unit 132.

Note that, for example, when a near-field communication function such as Bluetooth (registered trademark) is used, communication is also possible between the brainwave measurement unit 142 or the ocular muscle potential measurement unit 143 on the side of the head-mounted display 140 and the assessment information transmission unit 133 on the side of the smartphone 410.

By setting the near-field communication function in the head-mounted display 140 and the smartphone 410, it is possible to transmit and receive various signals between both the devices without executing wired connection.

[7. Process to which Feedback Information is Applied (Embodiment 6)]

Next, a process example to which the feedback information is applied will be described with reference to FIG. 11 and the subsequent drawings according to Embodiment 6.

In the information processing systems described in Embodiment 1 to Embodiment 5, on the basis of the content analysis result, the content analysis unit 150 outputs the feedback information 176 to the content delivery unit 120.

Embodiment 6 to be described below is an embodiment to which the feedback information is applied.

Figure 11:
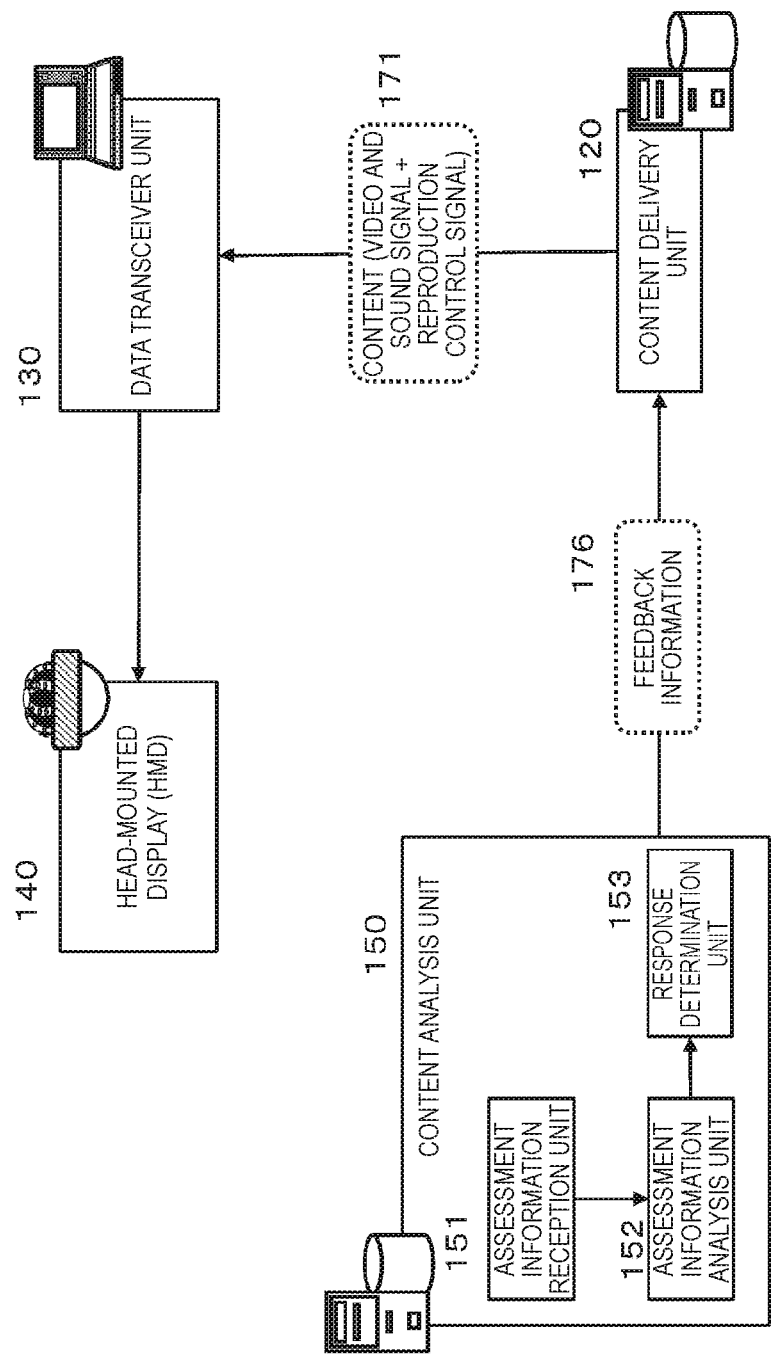
FIG. 11 is an explanatory diagram illustrating a configuration example of an information processing system according to the present disclosure.

As illustrated in FIG. 11, in all the information processing systems described in Embodiment 1 to Embodiment 5, the feedback information 176 is output to the content delivery unit 120 on the basis of the content analysis result in the content analysis unit 150.

The content delivery unit 120 can change setting of the content 171 to be provided to the user on the basis of the feedback information 176 input from the content analysis unit 150.

For example, on the basis of feedback information A from user A (viewer A), content or a scene estimated to highly attract user A is selected and delivered to user A. In addition, on the basis of feedback information B from user B (viewer B), content or a scene estimated to highly attract user B is selected and delivered to user B. In this way, content control corresponding to the user can also be executed.

Figure 12:
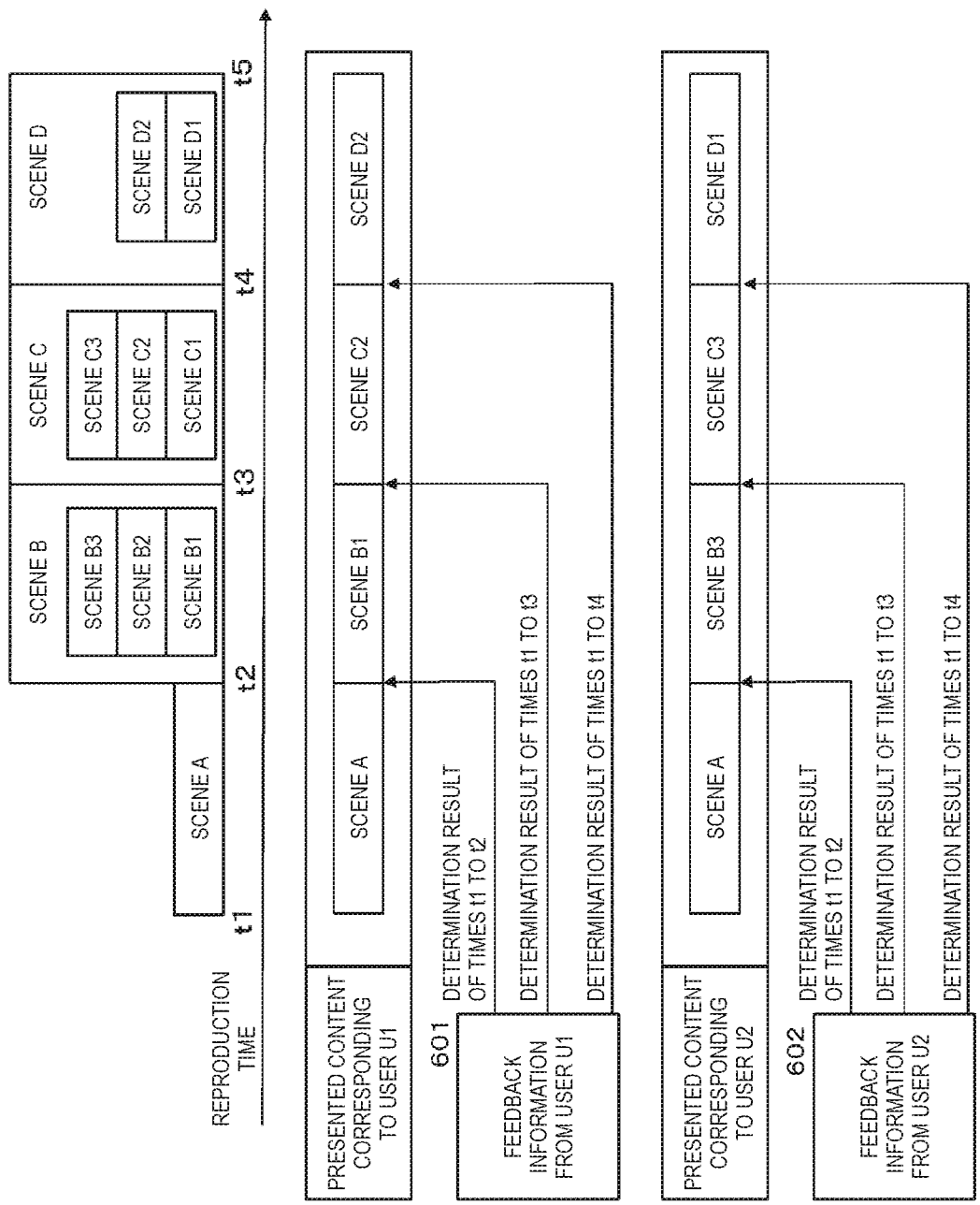
FIG. 12 is an explanatory diagram illustrating a delivery control example of content to which feedback information is applied.

FIG. 12 is a diagram illustrating content delivery control examples corresponding to users.

The content analysis unit 150 generates feedback information 601 and feedback information 602 including information for specifying content or a scene estimated to highly attract each of users U1 and U2 on the basis of the analysis result of the brainwave signal of each of users U1 and U2 acquired from users U1 and U2 and outputs the feedback information 601 and feedback information 602 to the content delivery unit 120.

The content delivery unit 120 selects content or scene information estimated to highly attract user U1 on the basis of the feedback information 601 from user U1 and transmits the content or the scene information to user U1.

In addition, the content delivery unit 120 selects content or scene information estimated to highly attract user U2 on the basis of the feedback information 602 from user U2 and transmits the content or the scene information to user U2.

In the example illustrated in FIG. 12, for video and sound signals retained in the content delivery unit 120, four scenes A, B, C, and D are largely configured. A reproduction time of each scene is as follows:

in scene A, time t1 to time t2;
in scene B, time t2 to time t3;
in scene C, time t3 to time t4; and
in scene D, time t4 to time t5.

The foregoing reproduction times are set.

Of the scenes, scene A includes only one scene, but scene B include sub-scenes B1, B2, and B3, scene C includes sub-scenes C1, C2, and C3, and scene D includes sub-scenes D1 and D2.

The content delivery unit 120 decides to select a sub-scene in the selectable scenes B, C, and D on the basis of the feedback information 601 and 602 from each user.

In the process of selecting a sub-scene of scene B, the feedback information of each of users U1 and U2 with regard to scene A from time t1 to time t2 is used.

On the basis of the feedback information of each of users U1 and U2 with regard to scene A from time t1 to time t2, a sub-scene estimated to highly attract each user is selected from sub-scenes B1 to B3 and the sub-scene corresponding to each user is delivered to each user.

In the process of selecting a sub-scene of scene C, the feedback information of each of users U1 and U2 with regard to scene A and scene B from time t1 to time t3 is used.

On the basis of the feedback information of each of users U1 and U2 with regard to scene A and scene B from time t1 to time t3, a sub-scene estimated to highly attract each user is selected from sub-scenes C1 to C3 and the sub-scene corresponding to each user is delivered to each user.

In the process of selecting a sub-scene of scene D, the feedback information of each of users U1 and U2 with regard to scene A, scene B, and scene C from time t1 to time t4 is used.

On the basis of the feedback information of each of users U1 and U2 with regard to scene A, scene B, and scene C from time t1 to time t4, a sub-scene estimated to highly attract each user is selected from sub-scenes D1 to D2 and the sub-scene corresponding to each user is delivered to each user.

Note that when scene C is selected, a determination result from time t2 to time t3 may be referred to. When the scene D is selected, a determination result from time t3 to time t4 may be referred to.

The example illustrated in FIG. 12 is an example in which sub-scene B1 is selected as scene B in consideration of the determination result of user U1 from time t1 to time t2, sub-scene C2 is selected as scene C in consideration of the determination result from time t1 to time t3, and sub-scene D2 is selected as scene D in consideration of the determination result from time t1 to time t4.

As a result, the video and sound signal presented to user U1 is a combination of scenes A, B1, C2, and D2.

Meanwhile, with regard to user U2, sub-scene B3 is selected as scene B in consideration of the determination result from time t1 to time t2, sub-scene C3 is selected as scene C in consideration of the determination result from time t1 to time t3, and sub-scene D1 is selected as scene D in consideration of the determination result from time t1 to time t4.

As a result, the video and sound signal presented to user U2 is a combination of scenes A, B3, C3, and D1.

In this way, the video and sound signal to be subsequently present can be adjusted for each user in consideration of a response of each user to the initially presented scene A.

That is, on the basis of the attraction or interest of each user estimated from a brainwave signal of the user, the content or the scene estimated to more highly attract each user can be selectively delivered to each user.

[8. Hardware Configuration Example of Information Processing Device]

Next, a configuration example of a hardware configuration of an information processing device configured as each device of the head-mounted display (HMD) 140, the data transceiver unit 130, the content analysis unit 150, the content delivery unit 120 described in the above-described embodiments will be described with reference to FIG. 13 and the subsequent drawing.

Figure 13:
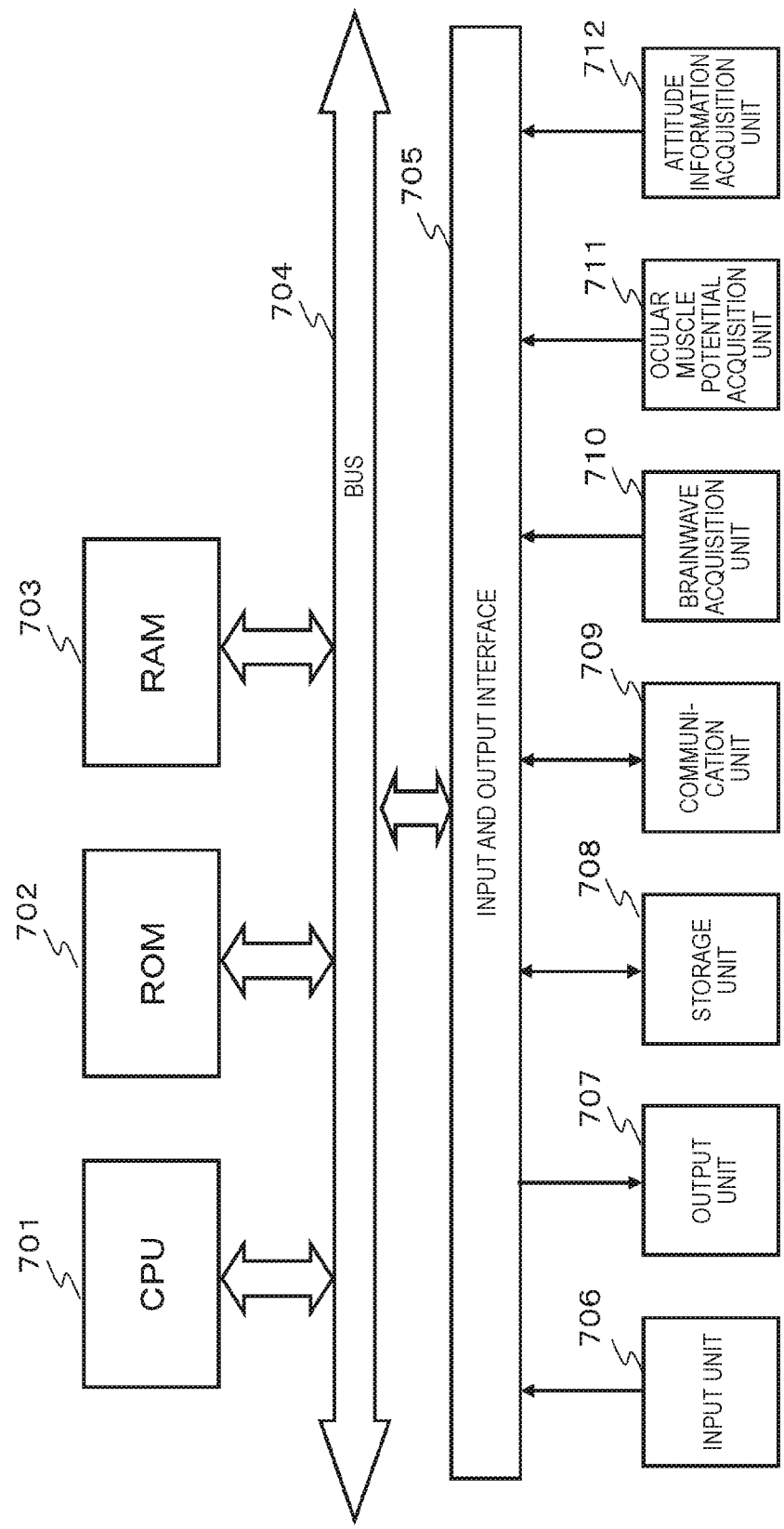
FIG. 13 is an explanatory diagram illustrating a hardware configuration example of an information processing device.

FIG. 13 is a diagram illustrating a configuration example of a hardware configuration of the head-mounted display (HMD) 140.

A central processing unit (CPU) 701 functions as a data processing unit that executes various processes in accordance with programs stored in a read-only memory (ROM) 702 or a storage unit 708. For example, the CPU 701 executes the processes in accordance with the sequences described in the above-described embodiments. A random access memory (RAM) 703 stores data or a program executed by the CPU 701. The CPU 701, the ROM 702, and the RAM 703 are connected to each other by a bus 704.

The CPU 701 is connected to an input and output interface 705 via the bus 704. An input unit 706 including any of various switches, a keyboard, a mouse, a microphone, or the like, an output unit 707 including a display, a speaker, or the like, are connected to the input and output interface 705. The CPU 701 executes various processes in response to instructions input from the input unit 706 and outputs processing results to, for example, the output unit 707.

The storage unit 708 connected to the input and output interface 705 includes, for example, a flash memory or the like and stores various kinds of data or programs to be executed by the CPU 701. The communication unit 709 functions as a data communication transceiver unit via a network such as near-field communication, the Internet, a local area network and communicates with an external device.

For example, a brainwave acquisition unit 710 acquires brainwaves via the disposed electrodes described above with reference to FIG. 3.

For example, an ocular muscle potential acquisition unit 711 acquires an ocular muscle potential via the disposed electrodes described above with reference to FIG. 5.

For example, an attitude information acquisition unit 712 includes a sensor such as an acceleration sensor or a gyro sensor and has a function of detection a motion or a change in an attitude of the user (viewer).

Figure 14:
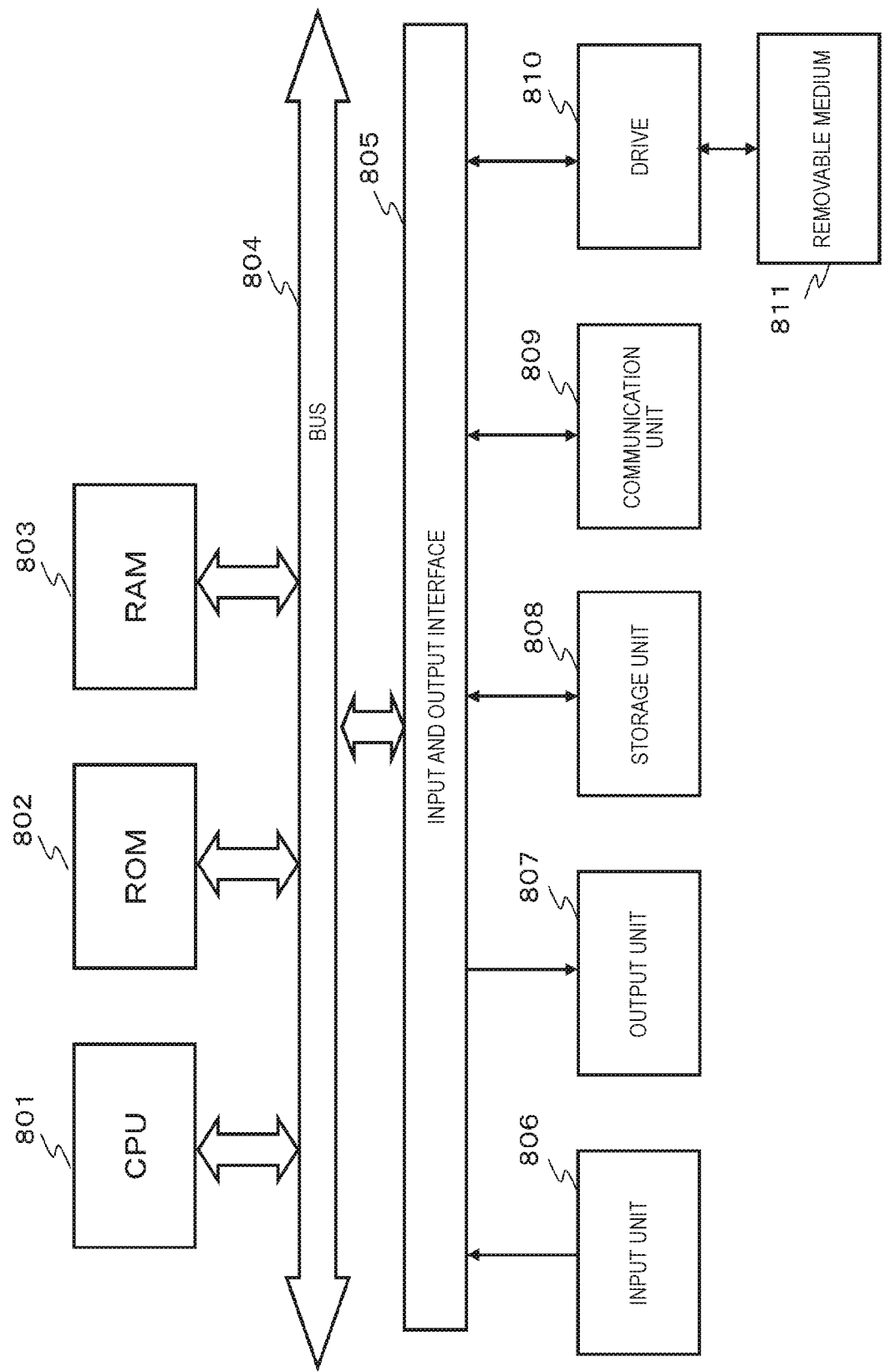
FIG. 14 is an explanatory diagram illustrating a hardware configuration example of an information processing device.

Next, a configuration example of a hardware configuration of an information processing device configured as each device of the data transceiver unit 130, the content analysis unit 150, the content delivery unit 120 will be described with reference to FIG. 14.

A central processing unit (CPU) 801 functions as a data processing unit that executes various processes in accordance with programs stored in a read-only memory (ROM) 802 or a storage unit 808. For example, the CPU 801 executes the processes in accordance with the sequences described in the above-described embodiments. A random access memory (RAM) 803 stores data or a program executed by the CPU 801. The CPU 801, the ROM 802, and the RAM 803 are connected to each other by a bus 804.

The CPU 801 is connected to an input and output interface 805 via the bus 804. An input unit 806 including any of various switches, a keyboard, a mouse, a microphone, or the like, an output unit 807 including a display, a speaker, or the like, are connected to the input and output interface 805. The CPU 801 executes various processes in response to instructions input from the input unit 806 and outputs processing results to, for example, the display unit 807.

The storage unit 808 connected to the input and output interface 805 includes, for example, a flash memory or the like and stores various kinds of data or programs to be executed by the CPU 801. The communication unit 809 functions as a data communication transceiver unit via a network such as near-field communication, the Internet, a local area network and communicates with an external device.

A drive 810 connected to the input and output interface 805 drives a removable medium 811 such as a magnetic disk, an optical disc, a magneto-optical disc, or a semiconductor memory such as a memory card to execute data recording or reading.

[9. Summary of Configuration of Present Disclosure]

The foregoing thus provides a detailed explanation of embodiments of the present disclosure with reference to specific embodiments. However, it is obvious that persons skilled in the art may make modifications and substitutions to these embodiments without departing from the gist of the present disclosure. In other words, the present disclosure has been disclosed by way of example, and should not be interpreted in a limited manner. The gist of the present disclosure should be determined in consideration of the claims.

Additionally, the present technology may also be configured as below.

(1)

An information processing device of a head-mounted display including:

an image presentation unit configured to present an image to a user (viewer); and a brainwave measurement unit configured to measure a brainwave of the user (viewer), in which a brainwave measurement electrode is set in a region of a head of the user (viewer) on which the head-mounted display is worn.

(2)

The information processing device according to (1), further including:

a sound output unit.

(3)

The information processing device according to (1) or (2), further including:

an ocular muscle potential measurement unit configured to detect an ocular muscle potential of the user (viewer) of the head-mounted display.

(4)

The information processing device according to (3), in which the ocular muscle potential measurement unit includes an ocular muscle potential measurement electrode in a region of the face of the user (viewer) in which the head-mounted display is worn.

(5)

The information processing device according to any of (1) to (4), further including:

an attitude detection unit configured to detect attitude information of the user (viewer) of the head-mounted display.

(6)

The information processing device according to (5), in which the attitude detection unit includes an acceleration sensor or a gyro.

(7)

An information processing device that generates assessment information set to enable identification of whether a brainwave signal is output when a certain image is presented in association with the brainwave signal acquired from a user (viewer) observing the image and reproduction control information of the image.

(8)

The information processing device according to (7), including:

a content reception unit configured to receive an image to be presented to the user (viewer) from outside, in which assessment information set to enable identification of whether a brainwave signal is output when a certain image is presented is generated using the reproduction control information received along with the image received through the content reception unit.

(9)

The information processing device according to any of (7) to (8), in which assessment information set to enable identification of whether an ocular muscle potential signal is output when a certain image is presented is further generated in association with the ocular muscle potential signal acquired from the user (viewer) observing the image and reproduction control information of the image.

(10)

An information processing device, in which a brainwave signal acquired from a user (viewer) observing an image and assessment information which is data corresponding to reproduction control information of the image and is set to enable identification of whether the brainwave signal is output when a certain image is presented are input, and an analysis process of acquiring a degree of interest in the image presented to the user (viewer) or at least one piece of information among assessment, a degree of concentration, and a degree of fatigue is executed using assessment information including the brainwave signal.

(11)

The information processing device according to (10), in which an ocular muscle potential signal acquired from the user (viewer) observing an image and assessment information which is data corresponding to reproduction control information of the image and is set enable identification of whether the ocular muscle potential signal is output when a certain image is presented are further input, and a region of interest in the image presented to the user (viewer) is analyzed.

(12)

The information processing device according to (10) or (11), in which attitude information acquired from the user (viewer) observing the image and assessment information which is data corresponding to reproduction control information of the image and is set to enable identification of whether the attitude information is output when a certain image is presented are further input, an electromyogram signal based on the attitude information is estimated, and a highly precise brainwave signal is generated by removing a noise signal equivalent to an electromyogram signal component from the brainwave signal and the analysis process is executed using the generated highly precise brainwave signal.

(13)

The information processing device according to any of (10) to (12), in which an analysis result obtained using the brainwave signal is further output as feedback information to a content delivery unit that delivers the image to the user (viewer).

(14)

An information processing device, in which image content to be presented to a user (viewer) is delivered, and control of the delivery content is executed in accordance with an analysis result based on a brainwave signal acquired from the user (viewer) observing an image.

(15)

The information processing device according to (14), in which delivery content control of the individual user (viewer) is executed on the basis of feedback information of the individual user (viewer).

(16)

An information processing system including:

a user device that presents content to a user (viewer); and a content analysis device that receives assessment information regarding the content from the user device and analyzes the assessment information, in which the user device generates assessment information set to enable identification of whether a brainwave signal is output when a certain image is presented in association with the brainwave signal acquired from the user (viewer) observing the image and reproduction control information of the image, and outputs the assessment information to the content analysis device.

(17)

The information processing system according to (16), in which the content analysis device executes an analysis process of acquiring a degree of interest in the image presented to the user (viewer) or at least one piece of information among assessment, a degree of concentration, and a degree of fatigue using assessment information including the brainwave signal, and a result of the analysis process is output as feedback information to the content delivery device that delivers the image to the user (viewer).

(18)

The information processing system according to (16) or (17), in which the user device generates assessment information set to enable identification of whether an ocular muscle potential signal is output when the certain image is presented in association with the ocular muscle potential signal acquired from the user (viewer) observing the image and reproduction control information of the image, and outputs the assessment information to the content analysis device, and the content analysis device analyzes a region of interest in the image presented to the user (viewer) using assessment information including the ocular muscle potential signal.

(19)

An information processing method executed in an information processing device, in which a data processing unit of the information processing device generates assessment information set to enable identification of whether a brainwave signal is output when a certain image is presented in association with the brainwave signal acquired from a user (viewer) observing the image and reproduction control information of the image.

(20)

A program causing an information processing device to execute information processing, in which the program causes a data processing unit of the information processing device to generate assessment information set to enable identification of whether a brainwave signal is output when a certain image is presented in association with the brainwave signal acquired from a user (viewer) observing the image and reproduction control information of the image.

In addition, the series of processes described in this specification can be executed by hardware, software, or a combination configuration of the hardware and the software. In a case in which a process is executed by software, a program that records a process sequence can be installed in a memory of a computer embedded in dedicated hardware to be executed or a program can be installed in a general-purpose computer capable of executing various processes to be executed. For example, the program can be recorded in advance on a recording medium. In addition to the installation on a computer from a recording medium, the program can also be received via a network such as a Local Area Network (LAN) or the Internet and can be installed on a recording medium such as a built-in hard disk.

Also, various processes described in this specification may be executed chronologically as described above and may also be executed in parallel or individually according to a processing capability of a device executing the processes or as necessary. Note that in this specification, the term "system" refers to a logical aggregate configuration of multiple devices, and the respective devices of the configuration are not limited to being inside the same housing.

INDUSTRIAL APPLICABILITY

According to an embodiment of the present disclosure, as described above, a configuration in which image assessment information is generated and analysis information such as the degree of interest in an image presented to the user or a region of interest is acquired on the basis of a brainwave signal of a user observing an image is realized.

Specifically, for example, a content delivery unit that delivers image content, a data transceiver unit that receives delivery content, a head-mounted display that presents content, and a content analysis unit that analyzes content assessment information are included. The data transceiver unit generates assessment information capable of identifying whether the brainwave signal is output when a certain image is presented in association with the brainwave signal and image reproduction control information acquired from the user and outputs the assessment information to a content analysis device. The content analysis device acquires analysis information such as the degree of interest in the image presented to the user or a region of interest using the brainwave signal.

In this configuration, a configuration in which the image assessment information is generated and analysis information such as the degree of interest in an image presented to the user or a region of interest is acquired on the basis of the brainwave signal of the user observing an image is realized.

REFERENCE SIGNS LIST 10 information processing system
20 content delivery unit
30 data transceiver unit
31 content reception unit
32 assessment information transmission unit
40 head-mounted display (HMD)
41 video and sound signal presentation unit
42 brainwave measurement unit
43 biometric information acquisition sensor
50 content analysis unit
51 assessment information reception unit
52 assessment information analysis unit
53 response determination unit
100 information processing system
120 content delivery unit
130 data transceiver unit
131 content reception unit
132 reproduction control signal retention unit
133 assessment information transmission unit
140 head-mounted display (HMD)
141 video and sound signal presentation unit
142 brainwave measurement unit
143 ocular muscle potential measurement unit
145 brainwave & ocular muscle potential detection electrode setting head-mounted display (HMD)
150 content analysis unit
151 assessment information reception unit
152 assessment information analysis unit
153 response determination unit
201 brainwave analysis unit
202 region-of-interest estimation unit
301 attitude detection unit
331 attitude-corresponding electromyogram signal estimation unit
701 CPU
702 ROM
703 RAM
704 bus
705 input and output interface
706 input unit
707 output unit
708 storage unit
709 communication unit
710 brainwave acquisition unit
711 ocular muscle potential acquisition unit
712 attitude information acquisition unit
801 CPU
802 ROM
803 RAM
804 bus
805 input and output interface
806 input unit
807 output unit
808 storage unit
809 communication unit
810 drive
811 removable medium

The invention claimed is:

1. An information processing device, comprising:
a central processing unit (CPU) configured to:
control reception of reproduction control information associated with image content, wherein
the image content includes a plurality of images, and
the image content is presented to a user;
receive a plurality of brainwave signals of the user acquired at a time of presentation of the image content; and
generate first assessment information that identifies to a brainwave signal of the plurality of brainwave signals that is output at a time of presentation of a certain image of the plurality of images, wherein the identification of the brainwave signal is based on a time code obtained from the reproduction control information, wherein
the time code is reproduction time information of the certain image.

2. The information processing device according to claim 1, wherein the CPU is further configured to control reception of the image content,
wherein
the reproduction control information further includes frame identification information and chapter information, and
the chapter information includes a scene change position of the image content.

3. The information processing device according to claim 1, wherein the CPU is further configured to:
receive an ocular muscle potential signal acquired at the time of the presentation of the certain image; and
generate second assessment information that identifies the ocular muscle potential signal that is output at the time of the presentation of the certain image, wherein the identification of the ocular muscle potential signal is based on the time code obtained from the reproduction control information.

4. An information processing device, comprising:
a central processing unit (CPU) configured to:
receive a brainwave signal acquired from a user, wherein
the brainwave signal is acquired at a time of presentation of an image to the user, and
the image is associated with reproduction control information;
receive first assessment information that identifies the brainwave signal that is output at the time of the presentation of the image, wherein the identification of the brainwave signal is based on a time code obtained from the reproduction control information, and the time code is reproduction time information of the image; and analyze the first assessment information to acquire a degree of interest in the image and at least one of assessment, a degree of concentration, or a degree of fatigue of the user.

5. The information processing device according to claim 4, wherein the CPU is further configured to:

receive an ocular muscle potential signal from the user acquired at the time of the presentation of the image; and receive second assessment information that identifies the ocular muscle potential signal that is output at the time of the presentation of the image, wherein the identification of the ocular muscle potential signal is based on the time code obtained from the reproduction control information of the image; and estimate a region of interest in the image presented to the user based on the first assessment information and the second assessment information.

6. The information processing device according to claim 4, further configured to:

receive attitude information from the user acquired at the time of the presentation of the image;

receive third assessment information that identifies the attitude information that is output at the time of the presentation of the image, wherein the identification of the attitude information is based on the time code obtained from the reproduction control information of the image;

estimate an electromyogram signal based on the attitude information;

generate a specific brainwave signal by removal of a noise signal equivalent to a component of the electromyogram signal from the brainwave signal; and analyze the degree of interest in the image and at least one of the assessment, the degree of concentration, or the degree of fatigue of the user based on nalysis the generated specific brainwave signal.

7. The information processing device according to claim 4, further configured to output an analysis result obtained based on the first assessment information as feedback information to a content delivery unit that delivers the image to the user.

8. An information processing device, comprising:
a central processing unit (CPU) configured to:
transmit image content, wherein
the image content is presented to a user,
the image content includes a plurality of images, and
assessment information that identifies a brainwave signal that is output at a time of presentation of a certain image of the plurality of images is generated;
receive feedback information based on the assessment information; and
control delivery of the plurality of images based on the feedback information such that a determined image of the plurality of images selected based on the feedback information is delivered to the user.

9. The information processing device according to claim 8, wherein the CPU is further configured to control the delivery of each of the plurality of images to each user of a plurality of users based on the feedback information of a respective user of the plurality of users.

10. An information processing system, comprising:
a user device configured to:
present image content to a user, wherein the image content is associated with reproduction control information, and the image content includes a plurality of images;
acquire a plurality of brainwave signals of the user at a time of presentation of the image content;
generate first assessment information that identifies a brainwave signal of the plurality of brainwave signals that is output at a time of presentation of a certain image of the plurality of images, wherein the identification of the brainwave signal is based on a time code obtained from the reproduction control information, wherein
the time code is reproduction time information of the certain image; and
output the first assessment information to a content analysis device; and
the content analysis device configured to:
receive the first assessment information from the user device; and
analyze the first assessment information.

11. The information processing system according to claim 10, further comprising a content delivery device, wherein the content analysis device is further configured to:
analyze the first assessment information to obtain a degree of interest in the certain image presented to the user and at least one of assessment, a degree of concentration, and a degree of fatigue of the user; and
output an analysis result as feedback information to the content delivery device,
wherein the content delivery device is configured to control delivery of the image content to the user based on the feedback information.

12. The information processing system according to claim 10, wherein
the user device is further configured to:
acquire an ocular muscle potential signal of the user acquired at the time of the presentation of the image content;
generate second assessment information that identifies the ocular muscle potential signal that is output at the time of the presentation of the certain image, based on the time code of the certain image obtained from the reproduction control information;
output the second assessment information to the content analysis device; and
the content analysis device is further configured to analyze a region of interest in the certain image presented to the user based on the second assessment information.

13. The information processing system according to claim 12, wherein the content analysis device is further configured to:
estimate a motion direction and a motion amount of eyeballs of the user based on the ocular muscle potential signal; and
generate region of interest information indicating the region of interest to the user in the certain image.

14. An information processing method, comprising:
in an information processing device:
controlling reception of reproduction control information associated with image content, wherein
the image content includes a plurality of images, and
the image content is presented to a user;
receiving a plurality of brainwave signals of the user acquired at a time of presentation of the image content; and generating assessment information that identifies a brainwave signal of the plurality of brainwave signals that is output at a time of presentation of a certain image of the plurality of images, wherein the identification of the brainwave signal is based on a time code obtained from the reproduction control information, wherein the time code is reproduction time information of the certain image.

15. A non-transitory computer-readable medium having stored thereon, computer-executable instructions which, when executed by a processor, cause the processor to execute operations, the operations comprising:

controlling reception of reproduction control information associated with image content, wherein
the image content includes a plurality of images, and
the image content is presented to a user;

receiving a plurality of brainwave signals of the user acquired at a time of presentation of the image content; and generating assessment information that identifies a brainwave signal of the plurality of brainwave signals that is output at a time of presentation of a certain image of the plurality of images, wherein the identification of the brainwave signal is based on a time code obtained from the reproduction control information, wherein the time code is reproduction time information of the certain image.

* * * * *